United States Patent [19]
Rhodes et al.

[11] Patent Number: 6,004,443
[45] Date of Patent: Dec. 21, 1999

[54] CHROMATOGRAPHY-FORMAT FLUID ELECTROPHORESIS

[76] Inventors: Percy H. Rhodes, 412 Westburg Ave.; Robert S. Snyder, 1515 Monte Sano Blvd., both of Huntsville, Ala. 35801

[21] Appl. No.: 08/910,225

[22] Filed: Aug. 13, 1997

[51] Int. Cl.$^6$ .................................................. G01N 27/26
[52] U.S. Cl. .......................... 204/454; 204/602; 204/601
[58] Field of Search ...................................... 204/450, 451, 204/454, 600, 601, 602; 73/864.34, 863.02, 863.03, 717, 705; 210/656

[56] References Cited

U.S. PATENT DOCUMENTS

| | | | |
|---|---|---|---|
| 3,762,208 | 10/1973 | Bice et al. | 73/721 |
| 4,160,600 | 7/1979 | Luke | 356/352 |
| 4,322,978 | 4/1982 | Fromm | 73/705 |
| 4,876,882 | 10/1989 | Yau | 73/54.09 |
| 5,355,714 | 10/1994 | Suzuki et al. | 73/146.5 |
| 5,482,608 | 1/1996 | Keely et al. | 204/452 |

OTHER PUBLICATIONS

Altria et al., "High Voltage Capillary Zone Electrophoresis: Operating Parameters Effects on Electroendosomotic Flows and Electrophoretic Mobilities", Chromatographia vol. 24, 1987, pp. 527–532.

Aris, "On the dispersion of a solute in a fluid flowing through a tube", Oxidation of Organic Sulphides, pp. 67–77.

Belen'Kii, "Chemical and physicochemical methods of analysis", Industrial Laboratory, vol. 59, No. 12, 1993, pp. 1063–1079.

Clifton, "Continuous–flow electrophoresis in the Taylor regime: a new possibility for preparative electrophoresis", Journal of Chromatography A. 757 (1997) pp. 193–202.

Cooke, "Multicapillary Columns: An Idea Whose Time Has Come", Today's Chemist at Work, Jan. 1996, pp. 16–20.

Davis, "Influence of thermal variation of diffusion coefficient on non–equilibrium plate height in capillary zone electrophoresis", Journal of Chromatography, 517 (1990), pp. 521–547.

Giddings, "Generation of Variance, Theoretical Plates, Resolution and Peak Capacity in Electrophoresis and Sedimentation", Separation Science, 4(3), Jun. 1969, pp. 181–189.

Gobie et al., "Theraml model of capillary electorphoresis and a method for counteracting thermal band broadening", Journal of Chromatography, 516 (1990), pp. 191–210.

(List continued on next page.)

*Primary Examiner*—Terrence R. Till
*Assistant Examiner*—Alex Noguerola
*Attorney, Agent, or Firm*—Larson & Taylor

[57] ABSTRACT

A novel free-fluid electrophoresis system applicable to both "analytical" and "preparative" separations combines the advantages of electrophoresis with those of automated liquid chromatography. The system attains plug flow of sample molecules within a separation column that has a sufficiently small diameter to avoid uncorrected convective dispersions and a sufficiently large diameter to ensure adequate preparative throughput. Sample molecules are introduced by liquid chromatographic-type injection mechanisms and moved to the separation column by means of a highly accurate, low-pressure pumping system. A novel pressure detector monitors pressure across the column during the electrophoretic separation. When the pressure across the column is zero, electroosmotic flow within the column exactly balances pump-induced flow so that there is no lateral dispersion of the separating sample molecules (i.e., plug flow is achieved). The pressure detector is monitored by a computer that controls either the pump and/or the electrophoretic power supply to maintain balance between the pressure-driven flow and the electroosmotically driven flow; alternatively carefully controlled departures from the balance can be maintained to increase throughput. The separated sample molecules can be optically detected within the separation column. When the separated sample molecules leave the separation column, they can be collected using fraction collection equipment similar to that used in liquid chromatography. The use of programmed nonuniform voltage and temperature fields allow for practically unlimited scale-up potential.

33 Claims, 15 Drawing Sheets

OTHER PUBLICATIONS

Gordon et al., "Protocol for Resolving Protein Mixtures in Capillary Zone Electrophoresis", Analytical Chemistry, vol. 63, No. 1, Jan. 1, 1991, pp. 69–72.

Grushka et al., "Effect of Temperature Gradients on the Efficiency of Capillary Zone Electrophoresis Separations", Analytical Chemistry, 1989, pp. 241–246.

Hjerten, "Free Zone Electrophoresis", Chromatog. Rev. 9, (1967), pp. 122–219.

Ivory, "The Prospects for Large–Scale Electrophoresis", Separation Science and Technology, 23(8&9), 1988, pp. 875–912.

Jorgenson et al., "Capillary Zone Electrophoresis", Science, vol. 222, Oct. 21, 1983, pp. 266–272.

Knox, "Thermal Effects and Band Spreading in Capillary Elector–Separation", Chromatographia, vol. 26, (1988), pp. 329–337.

Knox et al., "Miniaturisation in Pressure and Electroendosmotically Driven Liquid Chromatography: Some Theoretical Considerations", Chromatographia, vol. 24, 1987, pp. 135–143.

Landers, "Handbook of Capillary Electrophoresis", CRC Handbook of Capillary Electrophoresis: A Practical Approach, 1994, pp. 620–623.

Mikkers et al., "Concentration Distributions in Free Zone Electrophoresis", Journal of Chromatography, 169 (1979), pp. 1–10.

Potocek et al., "Electroosmosis in capillary zone electrophoresis with non–uniform zeta potential", Journal of Chromatography A, 709 (1995), pp. 51–62.

Roberts et al., "Dispersion Effects in Capillary Zone Electrophoresis", Journal of Chromatography, 480 (1989), pp. 35–67.

Rose et al., "Fraction Collector for Capillary Zone Electrophoresis", Journal of Chromatography, 438 (1988), pp. 23–34.

Taylor, "Dispersion of soluble matter in solvent flowing slowly through a tube", pp. 186–202.

Weinberger, "Separation solutions", American Laboratory, Mar. 1995, pp. 33U–V.

Zhu et al., "High–Voltage Capillary Zone Electrophoresis of Red Blood Cells", Journal of Chromatography, 470 (1989), pp. 251–260.

Culbertson et al. ("Flow Counterbalanced Capillary Electrophoresis", Anal. Chem. 1994, 66, 955–962).

Knox et al. ("Miniaturisation in Pressure and Electroendosmotically Driven Liquid Chromatography: Some theoretical Considerations", Chromatographia, 24, 1987, 135–1470).

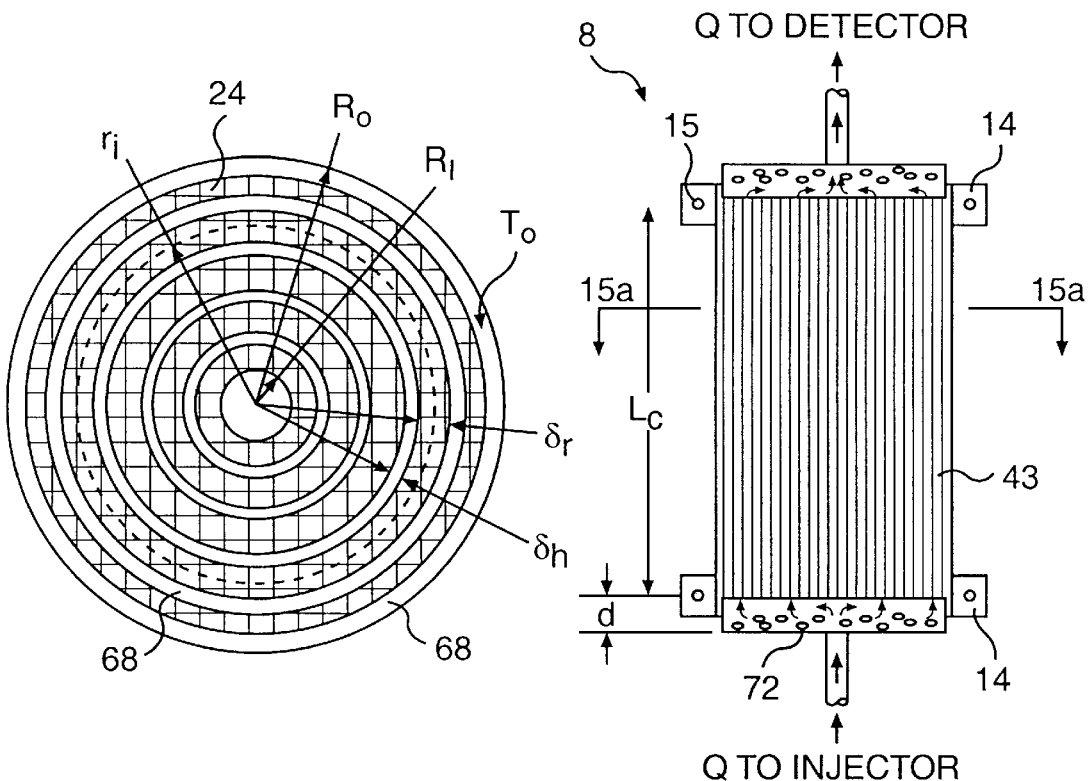
FIG. 15a
FIG. 15b
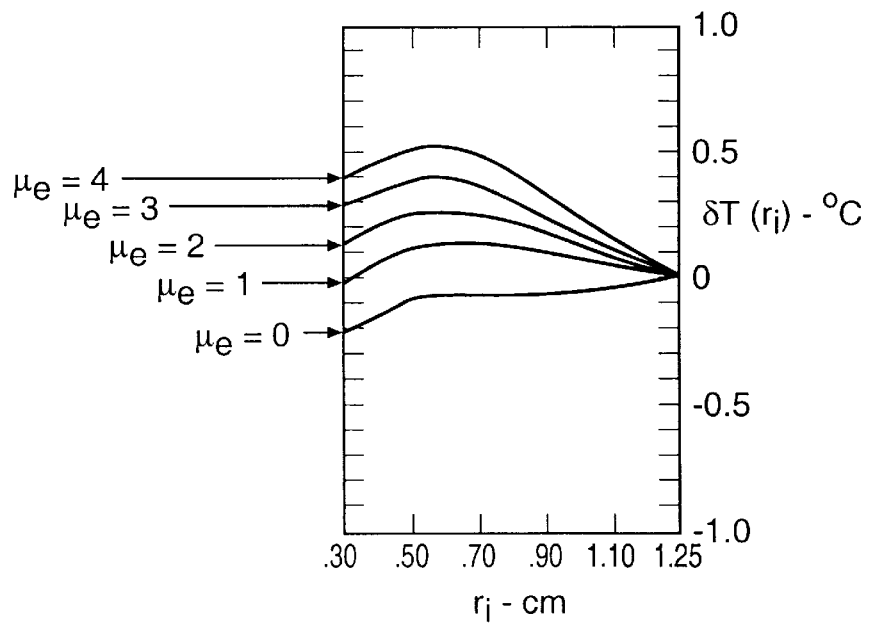
FIG. 16

CHROMATOGRAPHY-FORMAT FLUID ELECTROPHORESIS

BACKGROUND OF THE INVENTION

1. Field of the Invention

The general field of this invention is that of free-fluid electrophoresis. More specifically, the invention concerns the combination of the high separation efficiency of capillary zone electrophoresis (CZE) with the high operational efficiency similar to high performance liquid chromatography (HPLC) to create a new computer-controlled separation process, namely chromatography-format fluid electrophoresis (CFFE).

2. Description of Related Art

The primary technologies used for high-resolution separation of biological proteins and macromolecules have been variations of either chromatography or electrophoresis. In chromatography, separation occurs because of selective interactions between sample molecules and the fluid or solid phases through which the fluid sample is transported by either gravity or pressure. In electrophoresis an electrical field is used to impart motion to electrically charged sample molecules which then separate according to their mobility.

Early in the 20th century a Russian botanist, Mikhail Tswett, first developed chromatographic techniques to separate plant pigments. Chromatography has since evolved into techniques as diverse as one- and two-dimensional thin layer chromatography and various forms of liquid chromatography (LC), e.g., adsorption, affinity, ion exchange, gel permeation, and size exclusion. This wide variety of available techniques reflects the lack of a single instrument or method that satisfies the needs of the entire scientific community. When the research scientist wants a sample purified and/or analyzed, the method of choice is established based upon either past experience with similar samples or the result of trial and error with the wide variety of devices in the laboratory.

A number of chromatography variants have evolved because of the wide diversity of sample molecules and compatible liquid environments. For example, ion exchange chromatography is capable of separating molecules differing by very small differences in charge, depending upon ionic interactions with the media through which they pass. Affinity chromatography is a special type of adsorption chromatography in which the molecule to be analyzed or purified is specifically and reversibly adsorbed to a complimentary binding site on an insoluble porous solid substructure, the matrix. A change in solvent conditions may be used later to release the bound molecules.

Speed of chromatographic separation is second in importance only to the resolution of the separation; increased speed can be achieved by driving the solute through the matrix at a higher velocity than normal gravity-induced sedimentation. Generally the solute is driven by applying a high pressure, hence the name high pressure LC, an early name for the method now called HPLC which has evolved into the method of choice for high-resolution fractionation of biological materials. The development and optimization of HPLC was led by chemists who appreciated the overall versatility and flexibility of chromatography and who were experienced with both LC and thin layer chromatography. Although these scientists also had access to gel electrophoresis, HPLC identified and solved the major difficulties surrounding requirements for increased quantities of purified products.

Although, currently, electrophoresis is absolutely critical for certain analysis such as that involved in gene sequencing, it is generally much less popular than chromatography, especially for preparative separations. A major drawback to electrophoresis has been ohmic heating caused by the current flow and the resulting thermal degradation or disruption of the separation process. Early attempts at fluid electrophoresis date back to Reuss in 1807 and were greatly hampered by thermal convection. Modern electrophoresis was developed as an analytical and preparative technique by Arne Tiselius in 1937.

However, electrophoresis did not become practical and popular until a matrix was introduced to limit convective mixing. First, paper-based electrophoresis was used in the 1950's to elucidate the biochemical pathways of carbon fixation in green plants. In the 1960's electrophoresis in a gel matrix was introduced in starch, agarose, and polyacrylamide forms and quickly revolutionized protein biochemistry. In gel electrophoresis the electric field simply serves to move the sample through the gel matrix while the sieving effect of the matrix eliminates convection and improves the separation. Therefore, strictly speaking, gel electrophoresis is a hybrid between electrophoresis and chromatography with the matrix being responsible for at least part of the resolution of the separation. Gels with highly uniform pore structure provide size exclusion (i.e., separation based on molecular size) as well as limiting flows due to thermal convection. Isoelectric focusing, which takes advantage of the molecular mobility dependence on pH, combined with "ordinary" electrophoresis as a two-dimensional analog of thin layer chromatography has been an important analytical diagnostic technique.

Historically most separation processes, both chromatographic and electrophoretic, have been carried out in a supporting matrix which also served as the discriminator producing the separation. It must be kept in mind that matrix-based electrophoretic techniques generally combined chromatographic separation with true electrophoresis. However, the disruptive effects of thermal convection in free-fluid electrophoresis have been exaggerated. Although Hjertén's[11] classic 1967 work is often cited as an indictment of thermal convection, Hjertén employed rotation of his separation tube to control sedimentation, not thermal convection. HPLC, a largely free-fluid separation, has sidestepped the problem of thermal convection for the most part, since there is very little heating associated with fluid flow. On the other hand, electrochromatography is similar to gel electrophoresis in that considerable ohmic heating is developed but the packing material (matrix) is sufficiently restrictive to preclude convective mixing[12].

Like chromatography electrophoresis has also been used on a preparative scale. Preparative electrophoresis began when electrophoresis on filter paper was operated vertically and the dripping separands were collected over time. Exchanging a thin flowing liquid curtain for the paper removed the size exclusion advantage of the paper but improved the overall unrestricted separation of the separand molecules. "Continuous flow" electrophoresis grew from initial systems in 1960 until newer methods, such as HPLC, were shown to be easier to operate. With the perfection of HPLC, continuous flow electrophoresis declined from being the primary system for purification and collection of proteins and cells to a minor system used only in highly specialized cases, relying on older equipment that is no longer even manufactured.

During the 1970's, a number of electrophoresis systems with vertical cylindrical columns were developed to accomplish preparative batch separations. The separations took place in a thin annular part of the column since the central core and outer surface were cooled to minimize heat build-up. Density gradients of various high molecular weight gel polymers were frequently added to stabilize the migrating bands against thermal convection.

Although electrophoresis is conceptually simpler, chromatography has generally won the popularity contest. The reigning monarch of chromatography is HPLC which is capable of both sensitive analytic separations as well as preparative scale separations. No single analog to HPLC has thus far evolved in electrophoretic separations, although specific apparatus is available for some applications. CZE, the latest electrophoretic method to challenge HPLC, solves the problem of thermal mixing by making the separation column diameter so small that the wall effectively dampens appreciable thermal mixing. Also, the column cross section is so small that thermal gradients are kept very small.

In CZE the buffer and separation molecules are transported through the capillary by a process known as electroosmosis. When an electric field is applied to the filled capillary, the fluid will move relative to the charged inner surface. The cause of the charged inner wall of the capillary is ionization, ion adsorption, and/or ion dissolution due to contact with a polar medium. This wall condition can be described by a zeta potential. This inner surface charge is nominally negative in the presence of common aqueous buffers. Pharmaceuticals and proteins are frequently positively charged because of their pervasive amino functionality. The hydrated positive ions (counter-ions) at the wall move under the action of the electric field and through viscosity, causing a plug-type flow in the separation chamber (capillary). Unfortunately, positive sample species are also attracted to the negatively charged walls which can cause nonuniform wall zeta potential and hence an unpredictable electroosmotic (EOF) or "wall mobility."

CZE has now found a small niche due to its high resolving power and automated operation. Extremely small samples can be precisely separated by CZE in narrow-bore glass tubing—a significant advantage to those with only small, expensive, or scarce samples, CZE systems have found a market for drug testing and forensic applications and the "high end" equipment is now characterized as "high performance capillary electrophoresis."

In the analytical range CZE is considered superior, but attempts to provide CZE with preparative abilities, i.e., the capability of collecting useful quantities of separated samples[20] has yielded, at best, a tedious collection scheme not suited to commercial application. A major advantage of chromatography continues to be flexibility and versatility provided by a wide range of different columns and internal packings that can be adapted to a single front end (i.e., sampler/buffer insertion apparatus) and back end (i.e., detection, and fraction collection devices). However, this improved flexibility does come at a rather high system price.

The major disadvantage of chromatography is the necessity to obtain or find optimum adsorption materials to get the best resolution for a given separation. The power of affinity chromatography relies on highly specific interactions between the porous column matrix and the sample molecules. Ion exchange chromatography uses an insoluble matrix to which various charge groups are attached. The actual separation requires very selective sample attachment (adsorption) and detachment (desorption) from the matrix as different solutions are passed through the column. Thus, many chromatographic separations can be optimized only when molecular-specific interactions have been identified, matrix material manufactured, tested, and protocol for elution has been confirmed. Therefore, efforts to optimize the system can become very significant research tasks in themselves.

An additional problem with chromatographic separations of biological material is loss of biological activity. Close contact and physical/chemical interaction of the sample with the stationary phase provides a constant danger of less of biological activity (i.e., denaturation) as well as the significant possibility of irreversible adsorption of the sample to the chromatographic medium. Also, the use of the supporting matrix in HPLC leads to problems including "eddy migration" and adsorption interactions affecting resolution and separation time. For high resolution, HPLC suffers inherently from external (to the column) processes such as detection and injection; i.e., after injection the sample zone is subjected to hydrodynamic dispersion in the connecting tubing, and similar dispersion occurs when the separated zones leave the column on their way to the detector. In preparative HPLC the very high pressures necessary to ensure adequate throughput cause the stationary phase to deform or "slump." Also, due to the large pressure drop incurred by the column, the height-to-diameter ratio is small, often leading to unequal migration paths for the sample moving through the column.

Electrophoresis in thin layer gels is the world-wide standard for hospitals and diagnostic laboratories because of ease of operation and low cost of equipment. Medical technicians in hospitals and clinics use thin layer gel electrophoresis for the routine, standard analysis of body fluids. When properly stained and stored, the gels identify abnormal molecules and their relative quantity. A problem with gels is their lack of resolving power since gels can only be used to identify those proteins which bind the stain. Also, modern gel electrophoresis is an accumulation, for the most part, of manually intensive methodologies that cannot be run unattended and that cannot be readily automated: casting gels, applying samples, running gels, and staining gels are time-consuming tasks prone to irreproducibility and poor quantitative accuracy.

To electrophoretically distinguish the proteins and macromolecules not readily detected on gels, one must use CZE. An average commercial CZE system costs more than 20 times a typical gel electrophoresis system but will identify more than 20 times the number of subfractions under ideal conditions. Capillary systems now incorporate a variety of coatings and packing materials in their narrow bore (<100 $\mu$m) columns and separations of some mixtures of pharmaceutical interest have been resolved to the point that all molecules of interest have been identified. The small sample sizes (nanograms) can be an advantage if cost and availability limit the sample but are a disadvantage if further analysis of separated subfractions is necessary. The collection of subfractions is neither feasible nor practical with the presently available commercial units.

Reproducibility is an important factor in separations, especially analytical. In some cases it may be more important than resolution. Since the capillaries used in CZE are usually <100 $\mu$m in diameter, significant adsorption of the sample frequently takes place. This adsorption not only affects reproducibility but also resolution. As sample material coats the capillary walls, a nonuniform wall zeta potential results. This phenomenon has been investigated[18] where it was shown that plug flow in a capillary cannot be expected in cases where nonuniform wall mobilities exist, and further, that a nonuniform zeta potential generally leads to significant dispersion of subfraction peaks. It was shown that the nonuniform wall mobilities induced both sample circulations and parabolic flows in the affected capillaries. These sample circulations were highly localized and were not considered as significant a cause of peak broadening as were parabolic flows. Dispersion effects in the free-fluid electrophoretic process has led to a necessary but rather onerous preoccupation with capillary wall conditions. Much money, time, and effort have been spent in the development of wall coatings which reduce adsorption and enhance reproducibility of results.

Many problems are also associated with the methods of sample injection used in CZE. In a 1989 article, Grushka and McCormick[10] point out these inadequacies. These authors found that the actual insertion of the capillary into or withdrawal of the capillary from the sample solution resulted in the extraneous injection of sample into the capillary. They also found that the injected core length can exceed the maximum value permitted for the realization of the high separation efficiency of CZE. They concluded that the extraneous injection length will be superimposed on both the electrokinetic and hydrostatic injection techniques resulting in total injection zone sizes which can be unacceptable in terms of plate heights. Thus, while "dunking" the capillary might be simple, it is also quite crude with respect to obtaining the injected zone most desirable for high resolution.

In summary, chromatography and electrophoresis have distinct but different advantages for the separation and purification of biological materials. Scientists have traditionally purchased, used, and discarded a variety of instruments claimed to improve the purity of their desired product. Some of these instruments have been used successively to provide a slight improvement at each stage. It is the objective of this patent to take advantage of the best features of each method combined with specific innovations and produce a single instrument which will satisfy a majority of users' needs.

OBJECTS AND SUMMARY OF THE INVENTION

It is a goal of the present invention to provide a new electrophoretic separation system that can be readily used for biological cells, proteins, or other large molecules to (1) separate all components in the mixture for either identification or collection, (2) accomplish the separation as rapidly and efficiently as possible, (3) assure operational reliability and reproducibility from day to day, and (4) use equipment that is as versatile, inexpensive, and simple to operate with sample injection and detection devices similar to those already used in HPLC.

Presently available equipment can only satisfy a few of these desires, thus a wide variety of instruments must be used to satisfy the divergent needs of most laboratories. It is a goal of the present invention to address all of the above items in a more versatile and efficient manner than that characterized by the current state of the art.

The principles of the present invention are appliable to both "analytical" and "preparative" separations. The goal of analytical separations is the identification of all of the separable fractions in a small (i.e., analytical) sample. Preparative separations require larger sample sizes since they permit fractionation and collection of the sample subspecies. In the past, preparative separations often sacrificed high resolution to collect significant (i.e., preparative) quantities of separated material for subsequent use. This degradation of preparative resolution is minimized in the present invention by novel manipulation of both the temperature and flow fields in the separation chamber.

These and other objectives are met by a novel free-fluid electrophoresis system in which plug flow of sample molecules occurs within a separation column that has a sufficiently small diameter to minimize thermal convection and a sufficiently large diameter to ensure preparative throughput. Sample molecules are introduced by liquid chromatographic-type injection mechanisms and moved to the separation column by means of a highly accurate, low-pressure pumping system. A novel pressure detector monitors pressure across the column during the electrophoretic separation. When the pressure across the column is zero, EOF exactly balances pump-induced flow so that there is a plug flow of separating sample molecules. The pressure detector controls either the pump or the electrophoretic power supply to maintain this balance or carefully controlled departures from this balance. The separate sample molecules can be optically detected. When the separated sample molecules leave the separation column, they can be collected using fraction collection equipment similar to that used in LC.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings:

FIG. 15 illustrates an alternative embodiment using a cylindrical separation chamber comprised of a plurality of capillaries that are rectangular in cross section;

FIG. 16 shows the radial temperature compensations versus mobility (mobility multiplied by $10^4$ in $cm^2/V$ sec) for the separation chamber of FIG. 15.

DETAILED DESCRIPTION OF THE PREFERRED EMBODIMENTS

Figure 1:
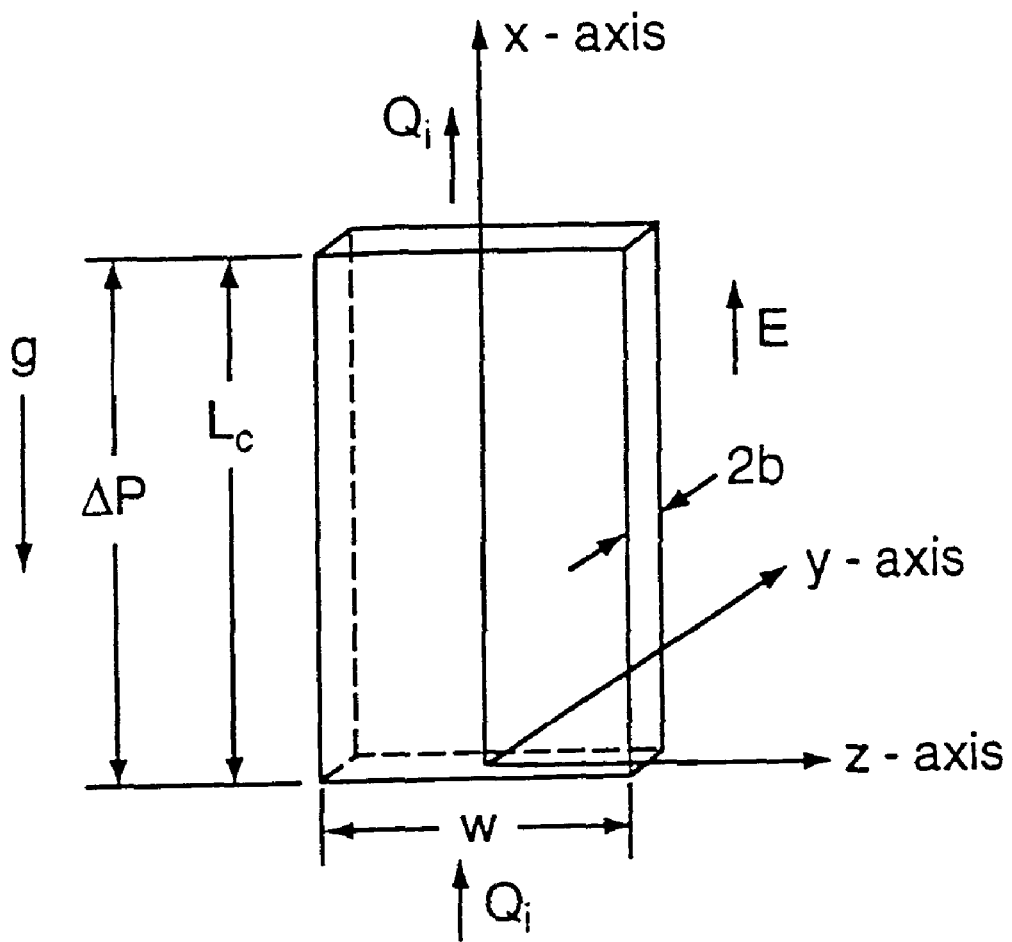
FIG. 1 shows a diagram of an idealized rectangular separation column wherein chamber width (w) is at least five times chamber thickness ($2b$)

The following description is provided to enable any person skilled in the art to make and use the invention and sets forth the best modes contemplated by the inventors for carrying out their invention. Various modifications, however, will remain readily apparent to those skilled in the art, since the general principles of the present invention have been defined herein, specifically to provide an electrophoretic method and apparatus wherein plug flow is produced during separation by balancing EOF against exogenously applied pressure.

The present invention achieves its goals through the new technique the inventors call chromatography-format fluid electrophoresis (CFFE). CFFE satisfies the great need for analytical and preparative separation of proteins and other biologically active soluble macromolecules. However, the method has no limitations that preclude separations of biological cells, colloids, and other particle dispersions although sample sizes larger than 1 gram will require some reconfiguration of the embodiments described herein. CFFE also has the capability of separating small molecules that comprise the majority of preparative and analytic separation requirements. The only requirement being that the sample molecules be electrically charged or be capable of being rendered charged.

The other goals concerning operation, reliability, and reproducibility are satisfied by the overall mechanical design of the apparatus. Although the primary system objective is high-resolution separation and collection of biological materials, the selected design must satisfy the ancillary requirements of the customer, e.g., ease of operation, reproducibility, and economy. The present instrument is planned to be a versatile, universal solution to a large variety of separation problems in medicine, industry, industry, and laboratory research.

In its simplest embodiment CFFE consists of a precision buffer pump connected to the inlet of an electrophoresis separation column, thereby producing an accurate and controllable flow in the column, thereby producing an accurate and controllable flow in the column during separation, as will be further explained below. This pressure-driven flow (PDF) would normally cause untenable flow dispersion in the separation column; however, positive control of this pressure-flow dispersion is achieved through the use of a novel flow transducer which assures plug flow in the separation chamber. A computer is used to monitor results and make necessary corrections to assure complete reproducibility.

Based on flow data from the control procedures, the computer can be programmed to control the process for maximum resolution, throughput, and reproducibility. A calibration run can be made using standard materials, and the results of the calibration run can be subsequently used by the computer to set parameters of chamber temperature and pump flow rate. These parameters control the sample mobility and flow in the chamber, respectively, and completely determine the sample residence time and, hence, reproducibility. Further, "on the fly" control by the computer can be made during a run by basing corrections on early peaks as they are eluted from the column.

Normally applying a PDF to the entrance of an electrophoretic separation chamber results in untenable flow dispersion which would completely negate the possibility of an electrophoretic separation. What must be appreciated to understand the present invention is that a fluid flow occurs during a free-fluid electrophoretic separation in the absence of any applied pressure. This flow is due to a phenomenon known as electroosmosis.

In an electrophoretic separation there is a movement of charged solute molecules within the separation chamber complicated by an interaction between the charged solute molecules and the chamber walls. Usually the chamber walls are constructed of glass or some similar material that has a net negative surface charge. This surface charge attracts a boundary layer of positive ions from the buffer, forming an electrical "double layer" along the liquid-wall interface. During an electrophoretic separation this excess of positive charge is attracted toward the cathode, causing an EOF of liquid along the interface. In the CFFE system EOF must be considered in conjunction with the PDF entering the chamber from the buffer pump. An imbalance in these flow rates affects the desired flat zone of separating sample, parabolically distorting it into a "smile" or a "frown," depending on which flow predominates. This flow imbalance causes a pressure difference along the chamber, detected by the pressure transducer, which in turn controls the electric field to increase or decrease the EOF and thereby produces flow balance.

The present inventors have determined, as demonstrated in detail below, that normal PDF rather than thermal effects (i.e., ohmic heating) is a dominant reason for using extremely narrow bore capillaries in free-fluid electrophoresis systems. This implies that larger capillaries may be used to reduce the multiple problems of sample adsorption in narrow capillaries. A necessary condition for this implementation would be a means to ensure control of PDFs which induce dispersion. The solution produced by the present inventors is a novel pressure transducer which allows precise balance of EOF in the separation chamber against pump-provided pressure flow. The balancing, achieved through the pressure transducer, assures plug flow during electrophoretic separation within the chamber. This precision flow allows the chamber inner dimension to be increased significantly over that presently required in CZE and, more importantly, allows the resulting system to operate in a true chromatographic format (i.e., ease of sample injection, detection, and collection). The relatively uncontrolled "electroosmotic pump" is replaced by a precision pump as in LC so that interactions with the chamber walls become a minor concern, thus ensuring complete reproducibility between runs.

For analytical applications, detection of the smallest amount of sample possible is the goal. Large column size allow larger sample volumes and possibly decreased sample concentrations which result in reduced electrokinetic problems as well as reduction of sample loss from handling. The larger size column also allows innovative design of in-line sample injectors that do not require electrophoretic stacking [22] to ensure compact sample injection zones, thereby eliminating complex buffer systems. This also permits the use of buffers with lower conductivities. On the detection end, the larger column sizes allow novel in-line optical detection designs with longer light path lengths. The separation column of the present invention is essentially straight, and supported in a vertical orientation. This configuration allows continuous analysis of the flows and dispersions in the chamber, as in HPLC, to provide data for control procedures implemented by the computer.

For preparative applications, more and higher sample concentrations are desirable in order to maximize throughput. Small ($\leq 100$-$\mu$m diameter) columns should be used to protect the high sample concentrations against buoyancy-induced instabilities. Individual columns (capillaries) may be grouped, or a multicolumn[5] array or section, which may be used to form a high-capacity composite column. With small column diameters, sample concentrations as high as 5% are possible, making the system comparable to HPLC in capacity. The CFFE concept allows preparative separations to be carried out in the manner of LC and also allows the use of LC components, i.e., injectors, detectors, and collection equipment.

COLUMN DIAMETER VERSUS THERMAL DISPERSION

The present invention greatly improves on CZE, particularly by providing preparative methodology. Part of this advance is due to use of a greater column diameter than is possible with CZE. Therefore, it is important to understand how the fluid column diameter relates to thermal convection. In the following treatment we will show that thermal convection is not a major factor when the column or separation chamber has a <300 $\mu$m inside diameter. The origin of thermal-induced dispersion lies with the mobility variation of the sample with temperature. Larger column bores produce a greater thermal gradient (dT) between the column center line and the periphery, as heat is conducted away at the chamber periphery, resulting in a temperature difference between the chamber center and its containment walls. Sample mobility and wall mobility (electroosmosis) vary with temperature causing a temperature-gradient-associated dispersion in the separation chamber. Temperature gradients will cause variation along the wall in the EOF and variations in the sample migration rates across the chamber.

There are two modes of convection in free-fluid electrophoresis systems such as CFFE or CZE—conventional convection and unstable convection. Conventional convection is initiated instantly by a temperature gradient normal to the gravity field direction, while unstable convection can occur when the temperature gradient is parallel to, but opposed to, the gravity vector. The onset of unstable convection is not immediate but depends strongly on the geometry of the electrophoretic chamber. In a vertical column, conventional convection occurs from the temperature difference between the column center and its periphery, while unstable convection occurs when a vertical temperature (density) gradient is imposed on the fluid with higher temperatures occurring at the lower end of the (vertical) separation chamber, so that heavier fluid is above lighter fluid. A related disturbance associated with unstable convection occurs when the sample zone is of a higher density than the carrier buffer. Generally, this density difference is due to a difference in sample concentration (i.e., the comparatively dense sample is concentrated in the sample zone).

We will look at conventional convection in a vertical separation chamber for the case of rectangular and cylindrical chambers. First, consider a rectangular column with an electric field impressed along its axis (see FIG. 1). Buffer flow $Q_i$ is in an upward (x direction) and the chamber is cooled by a coolant flow, also in the upward direction, thereby providing an increasing temperature on the chamber walls from the bottom up as the temperature of the coolant increases. It is assumed that the chamber is cooled uniformly in the z direction so that no lateral temperature gradients exist (this assumption is true when the chamber thickness (2b) is sufficiently small). Here, the chamber is thin enough so that the bulk of the heat is extracted along the broad side walls. Under these assumptions one-dimensional fluid motion exists in the chamber and the equation of motion and temperature distribution across the chamber thickness can be written as $$0 = -\frac{dp}{dx} + \rho g \beta \theta + \eta \frac{d^2 u}{dy^2}$$

and $$T - T_w = \theta = \delta T \left(1 - \frac{y^2}{b^2}\right)$$

where
  $\rho$=fluid density,
  $\beta$=thermal expansion coefficient
  $\eta$=fluid absolute viscosity,
  p=pressure, and
  $\delta T$=temperature difference between the center plane and the broad walls Combining the above equations produces $$0 = -\frac{dp}{dx} + \rho g \beta \delta T \left(1 - \frac{y^2}{b^2}\right) + \eta \frac{du^2}{dy^2}$$

and integrating two times with the boundary conditions
  at y=±b u=$V_w$=$\mu_w$E
and $$\text{at } y = 0 \quad \frac{du}{dy} = 0$$

where
  $\mu_w$=electroosmotic wall mobility,
  $V_w$=wall velocity, and
  E=electric field strength.

The solution to the above differential equation produces the following:

$$u = \left(1 - \frac{y^2}{b^2}\right)\left[-\frac{b^2}{2\eta}\frac{dp}{dx} + \frac{\rho g \beta \delta T b^2}{12\eta}\left(5 - \frac{y^2}{b^2}\right)\right] + V_w. \quad (1)$$

The buffer flow rate $Q_i$ is given by $$Q_i = w \int_{-b}^{b} u\, dy.$$

Substituting an u and integrating, we obtain the pressure gradient $$\frac{dp}{dx} = -\frac{3}{2}\frac{\eta}{b^3 w}(Q_i - 2bwV_w) + \frac{2}{5}\rho g \beta \delta T.$$

The nondimensional velocity $$U\left(= \frac{u}{V_w}\right)$$

is obtained by substitution of $$\frac{dp}{dx}$$

into equation (1)

$$U = \frac{u}{V_w} = \left(1 - \frac{y^2}{b^2}\right)\left[N_1 + 25N_2\left(1 - \frac{y^2}{5b^2}\right)\right] + 1. \quad (2)$$

Here we have used $$\delta T = \frac{E^2 b^2}{2\rho_o k} \text{ and } V_w = E\mu_w.$$

The temperature excess is determined by the balance of ohmic heating and diffusion. The wall velocity is determined by the wall mobility.

The dimensionless parameters $N_1$ and $N_2$ denote the magnitudes of the pressure and convective dispersions, respectively $$N_1 = -\frac{3}{4}\frac{(Q_i - 2bwV_w)}{bw\mu_w E} \text{ and } N_2 = \frac{\rho g\beta Eb^4}{120\eta\mu_w k\rho_o}.$$

To estimate the relative effect of these parameters, consider a typical condition for a single vertical column:

$L_c$=chamber length—50 cm
b=chamber half-thickness—0.019 cm,
E=chamber axial voltage gradient—150 V/cm,
β=thermal expansion at 25° C.—257×10$^{-6}$/° C.,
η=viscosity of water—0.01 gm/cm sec,
$\mu_w$=wall mobility—5.1×10$^{-4}$ cm²/V sec,
k=thermal conductivity—5.83×10$^{-3}$ W/° C. cm, and
$\rho_o$=electrical resistivity of buffer—1000 Ω cm
giving $$N_2 = 2.2 \times 10^{-6}.$$

Equation (1) may be rewritten as $$U = \left(1 - \frac{y^2}{b^2}\right)N_1\left[\left(1 + \frac{25N_2}{N_1}\right)\left(1 - \frac{y^2}{5b^2}\right)\right] + 1,$$

and the parameter $N_1$ can be obtained by comparing equation (1) and (2) as $$N_1 = \frac{-b^2}{2\eta\mu_w E}\frac{\Delta p}{L_c} \quad (3)$$

where $\Delta p$ is the pressure difference across a chamber length of $L_c$.

Then for any pressure difference $\Delta p$ there exists the parameter $N_1$ and the ratio $25\,N_2/N_1$ gives the relative influence of thermal convective dispersions compared to those produced by the pressure difference $\Delta p$. To not significantly influence the total flow, $25\,N_2/N_1$ should be small compared to 1, so consider the value of 0.10.

Setting $25\,N_2/N_1 = 0.1$, then
$N_1 = 0.0006$, or from equation (3), $\Delta p = 1.1 \times 10^{-5}$ cm of water.

This is a very small pressure difference. In practice, the uncontrolled pressure difference would be several orders of magnitude greater than this but thermal convection would still be insignificant compared to the hydrodynamic effect.

Another way to represent this relative effect is to substitute the definition of $N_1$ and $N_2$ into the ratio $25\,N_2/N_1$, so $$25\frac{N_2}{N_1} = \frac{5}{6}\frac{\beta\Delta T}{\left(\frac{\delta h}{L_c}\right)} = 0.10$$

where δh is the pressure difference between the column ends. Assume 0.05 cm of water for a conservative case, so ΔT=0.47° C. This is a huge ΔT for any capillary separation column and would produce unacceptable sample mobility dispersions; thus showing again that PDFs are of a far greater concern in vertical electrophoresis columns that convective flows.

This analysis was carried out in a vertical column where the thermal convection would be expected to cause much greater mixing than in a horizontal column where the circulations would be on a length scale of b. The results, however, show that even in this case the pressure difference between the column ends is the cause of dispersion, not thermal convection. The above calculated pressure difference Δp is very small and precise leveling of the column ends would be required to avoid it.

The foregoing results suggests that the improvement in separation performance by the use of "open" capillary tubes came not from the reduction of thermal convection, as the literature maintains, but only from the reduction of pressure-driven dispersion provided by the small column diameters used, i.e., <100 μm. That is, in small column diameters, PDF is damped by interaction between the fluid and the nearby walls.

Figure 2:
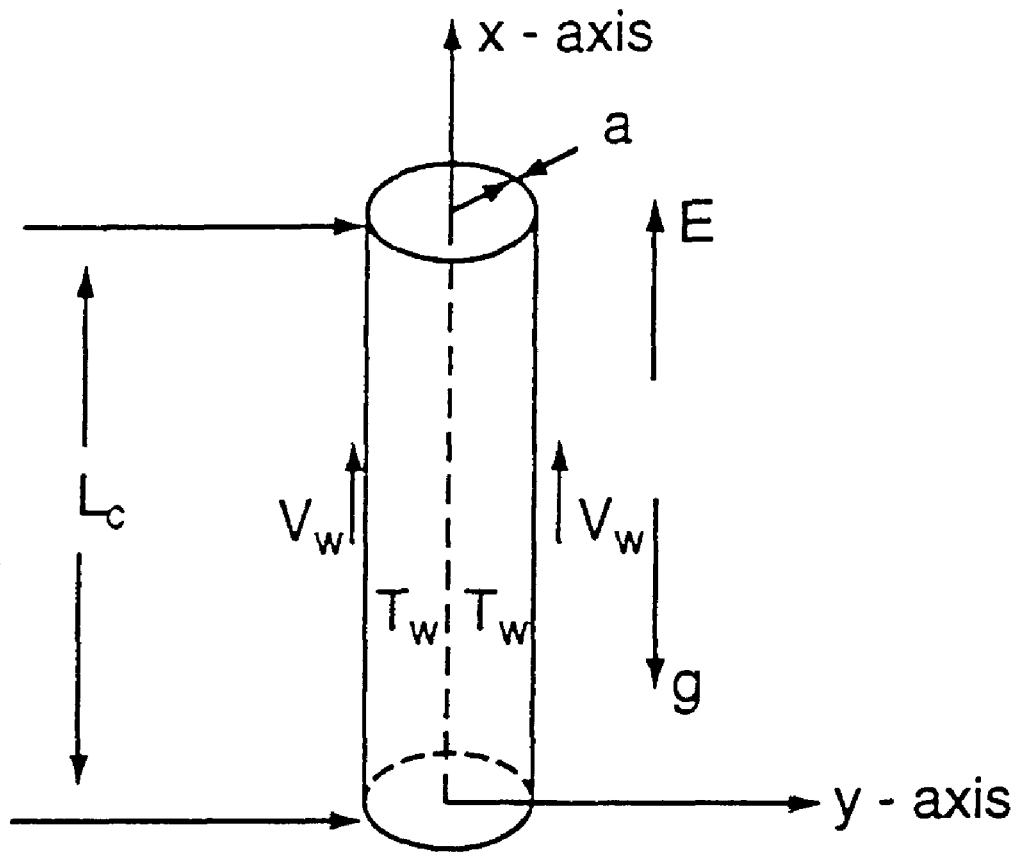
FIG. 2 shows a diagrammatic representation of a small capillary chamber having an inside diameter of 75 $\mu$m.

In a manner similar to the analysis carried out above, we can estimate the effect of thermal convection in a conventional capillary (dimensions and operation parameters commonly seen in the literature). Consider a vertical capillary, shown in FIG. 2, with radius α=0.0038 cm (75-μm inner diameter),
length $L_c$=50 cm
voltage gradient E=300 V/cm, and
fluid resistivity $\rho_o$=5000 Ω cm (conductivity=200 μMho).

The nondimensional velocity is given by $$U = \frac{1}{2}\left(1 - \frac{y^2}{a^2}\right)N_p\left[\left(1 + \frac{25N_c}{N_p}\right)\left(1 - \frac{y^2}{5a^2}\right)\right] + 1,$$

where $$N_p = -\frac{a^2\Delta p}{\eta\mu_w EL_c},$$

and $$N_c = -\frac{\rho g\beta Ea^4}{120\eta\mu_u k\rho_o}.$$

Here Δp is the pressure difference applied along the column and is not the static pressure between the ends of the vertical column. This qualification is necessary in order to conveniently analyze the thermal convective flows. Assume that reasonable practice would produce a difference of 0.3 cm of water. The dimensionless parameter ratio becomes so $N_p/N_c \approx 62{,}800$.

Although the hydrodynamic dispersion was taken to be 3 mm of water, the ratio of $N_p/N_c$ is more than four orders of magnitude, indicating again the insignificance of conventional thermal convection.

The foregoing estimate shows clearly that in a vertically oriented capillary the PDF is about four orders of magnitude greater than the thermal convective flow. If we now lay the capillary on its side, make an inverted U-bend, or coil it, then the convective effect will be reduced, owing to multiple circulations now produced. These circulations will be on the length scale of $\alpha$, while in the former case they were on the length scale of $L_c$. Also, these circulations can be opposite in rotation, and/or move the solute molecules to different radial positions and hence attenuate the level of disturbances. Having shown that the vertically oriented column is the worst case for convective flow, and with it being obvious that a PDF due to $\Delta p$ impressed across the column ends is the same whatever the orientation of the column, that is, $N_p/N_c$ is still on the order of $10^4$. Thus, the rationale for going to smaller bore capillaries in order to reduce thermal convection is in error.

CHAMBER TEMPERATURE PROFILE

The parabolic temperature profile[6] across the separation chamber results in a parabolic variation in the migration velocity of the sample as a function of position across the chamber cross section[8]. This parabolic distortion is mitigated by diffusion which spreads the sample band and tends to evenly distribute the sample molecules across the chamber cross section.

Sample mobilities change about $0.02/°$ C.[14] so that the equivalent mobility dispersion velocity can be obtained from the average mobility perturbation due to temperature.

The mean excess velocity is $\overline{\delta u} = 0.5\, \delta u_o$, where $\delta u_o$ is the difference between the migration velocity at the axis where the temperature is $t_o$ and at the wall where the temperature is $t_w$.

Thus the temperature difference $\delta T = t_o - t_w$ causes the mobility perturbation $\overline{\delta u}$.

$$\overline{\delta \mu} = \frac{1}{2}[(0.02)\delta T]\mu_w$$

where $\mu_w$ is the sample mobility at the wall. Then $\overline{\delta \mu}$ is the mobility perturbation which translates into the velocity disturbance and $$\frac{\overline{\delta u}}{\mu_w} = 0.01 \delta T.$$

The Taylor-Aris equation can be written in terms of plate height H, $$H = \frac{\sigma^2}{L_c} = \frac{\left(\frac{\overline{\delta u}}{\mu_w}\right)^2 d_c^2 u_w}{96 D_m} \tag{4}$$

where the variance $$\sigma^2 = \frac{L_c d_c^2 \overline{u}}{96 D_m}$$

is described in Knox and $D_m$ is the molecular diffusivity.

Combining equations and using the expression for temperature rise in a cylinder due to Joule heating $$\delta T = \frac{E^2 d_c^2}{16 k \rho},$$

equation (4) then becomes $$H_t = \frac{\sigma_x^2}{L} = \frac{(0.01)^2 E^4 d_c^6 \mu_w E}{96(16)^2 D_m k^2 \rho^2}.$$

Since $u_w = \mu_w E$ so, $$H_t = 2.034 \times 10^{-9} \frac{E^5 d_c^6 \mu_w}{k^2 \rho^2 D_m}. \tag{5}$$

It is important to note that the thermal distortion varies as the sixth power of the column diameter. We will use this result in making comparisons to other forms of dispersions.

From the preceding analysis the convective flow perturbation velocity is $$u = \frac{\rho g \beta E^2 a^4}{48 \eta k \rho_o}\left(1 - \frac{y^2}{a^2}\right)\left(5 - \frac{y^2}{a^2}\right).$$

The centerline velocity then is $$u_o = \frac{5 \rho g \beta E^2 a^4}{48 \eta k \rho_o} = \frac{5 \rho g \beta d_c^2}{768 \eta k \rho_o}.$$

The average perturbation velocity is $$\delta u = \frac{1}{2} u_o = \frac{5 \rho g \beta E^2 d_c^4}{1536 \eta k \rho_o}$$

$$\frac{\delta u}{u_w} = \frac{5 \rho g \beta E^2 d_c^4}{1536 \eta k \rho_o E \mu_w}.$$

The velocity profile distortion at the center line is $$\delta l = \delta u \tau \text{ and } \tau = \frac{Lc}{u_w}$$

$$\delta l = \frac{\delta u}{u_w} L_c.$$

From the Taylor equation we can then derive $$\sigma^2 = \frac{\left(\frac{\delta u}{u_w}\right) L_c d_c^2 \left(\frac{\delta u}{u_w}\right) u_w}{192 D} \tag{6}$$

and

-continued $$H_c = \frac{25\rho^2 g^2 \beta^2 E^4 d_c^8 d_c^2 E \mu_w}{192D(1536\eta k \rho_o E \mu_w)^2}$$

$$H_c = 5.5 \times 10^{-8} \frac{\rho^2 g^2 \beta^2 E^3 d_c^{10}}{\eta^2 k^2 \rho_o^2 \mu_w D}.$$

Comparing equation (5) and (6) we can see that thermal convective is negligible even for tubes as large as 800 μm. We have gone to some length to show that thermal convection does not, in itself, defeat free-fluid electrophoresis in wide-bore capillaries. While these discussions have all been analytical, there exists data to support these conclusions. In 1898 Zhu and Chen[23] separated red blood cells in a vertical capillary with an inner diameter of 450 μm. The bottom of the column was closed to flow and contained the positive electrode separated from the chamber by a membrane. The buffer conductivity was ~300 μMho and the voltage gradient 235 V/cm. These are similar conditions to those used in the foregoing analysis. The only problem discussed by these authors was a deterioration of the electrophoresis tubes (chambers) and an associated irreproducibility of results. There was no mention of any problems associated with thermal convection. Another comparison of equations (5) and (6) shows that increasing the voltage gradient E is much more likely to cause thermal dispersions than thermal convective dispersion.

SAMPLE DENSITY EFFECTS

If we orient the column vertically and flow buffer and coolant upward in a parallel flow arrangement, the temperature will increase up the column monotonically. Convection cannot occur because warmer fluid will always be above cooler fluid in the separation chamber. The sample zone concentration cannot be made so high that this condition of decreasing fluid density is compromised to the point that an instability will result. The restrictions on concentration required by the solutal Rayleigh number will ensure that this instability will not arise.

The sample solute will increase the density of the sample zone in relation to its solvent concentration. The condition is worse at the beginning of the separation and is mitigated as the injected zone separates electrophoretically into separate species zones. Whether or not unstable convection occurs under these conditions depends on the solutal Rayleigh number[21] which is given by $$Ra_s = \frac{\alpha g \left(\frac{\partial c}{\partial x}\right) a^4}{\eta D}$$

where $$\alpha \left(= \frac{\partial \rho}{\partial c}\right)$$

is the concentration densification coefficient, and D is the diffusion coefficient. Convection will always occur when $Ra_s > 67.94$. Consider a capillary with a 0.1-cm-thick zone of the protein lysozyme which has a molecular wt. of 14,000 Daltons.

a=capillary radius=0.0038 cm (76-μm inner diameter),
c=concentration=4.0×10⁻⁵ gm/cm³ (Gordon[9]),
α=0.056 gm/gm, $D=1\times10^{-7}$ cm²/sec,
δx=zone width=0.1 cm, and
$Ra_s=0.0092$ It can, therefore, be shown that in a typical CZE separation that buoyancy-induced convection of the sample zone is not a problem. It is possible to calculate the largest chamber diameter not subject to buoyancy-induced convection $$Ra_s = 67.94 = \frac{\alpha g \left(\frac{\delta c}{\delta \bar{x}}\right) a^4}{\eta D}$$

$$a^4 = \frac{67.94 \eta D}{\alpha g}\left(\frac{\delta \bar{x}}{\delta c}\right).$$

$a = 0.035$ cm $d = 0.070$ cm where $\delta \bar{x} = \delta x/2 = 0.05$ cm

This diameter is much too large even for use in a CFFE system where active control of hydrodynamic dispersion is exercised; therefore, concentration gradient-induced dispersion would not be a concern in analytical CFFE application with a smaller diameter.

The solutal Rayleigh number will, however, be the determining factor in preparative applications of CFFE. Since sample throughput is proportional to $\alpha^2$ while the limiting $Rs_a$ is proportional to $a^4$, it is advisable to increase sample concentration and reduce the column radius for maximum throughput. This may well necessitate the use of multiple tubular columns or multiple narrow rectangular chambers. However, the work of Taylor and others[2, 4, 21] in analyzing this instability has all been done on longer time scales than would be typical of separations being considered here. In some cases, therefore, additional analysis may be needed to optimize the proper balance of tube diameter and sample concentration giving the most efficient configuration for preparative CFFE.

PREFERRED EMBODIMENT

System Overview

Figure 3:
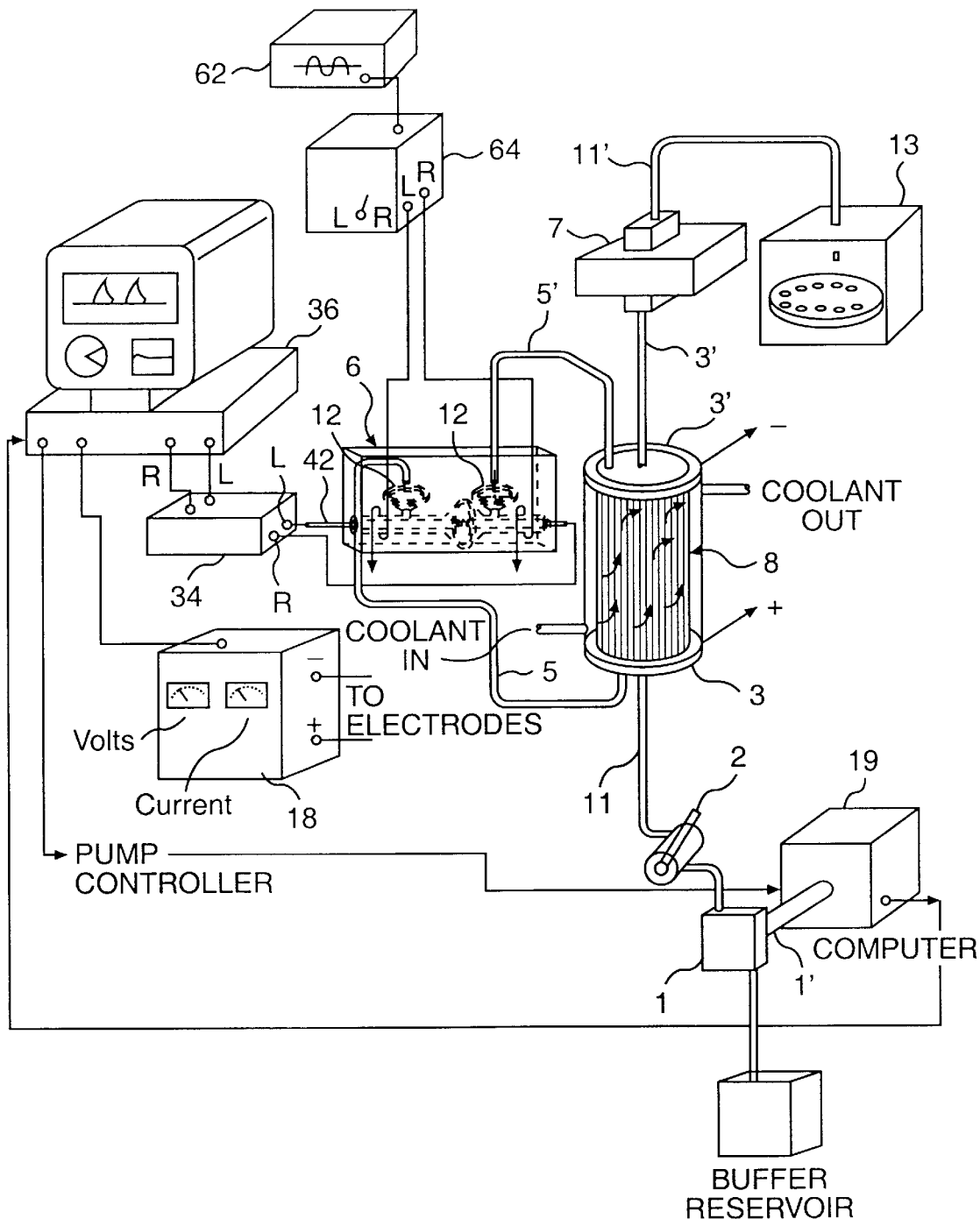
FIG. 3 shows the present invention as a preparative system.
Figure 4:
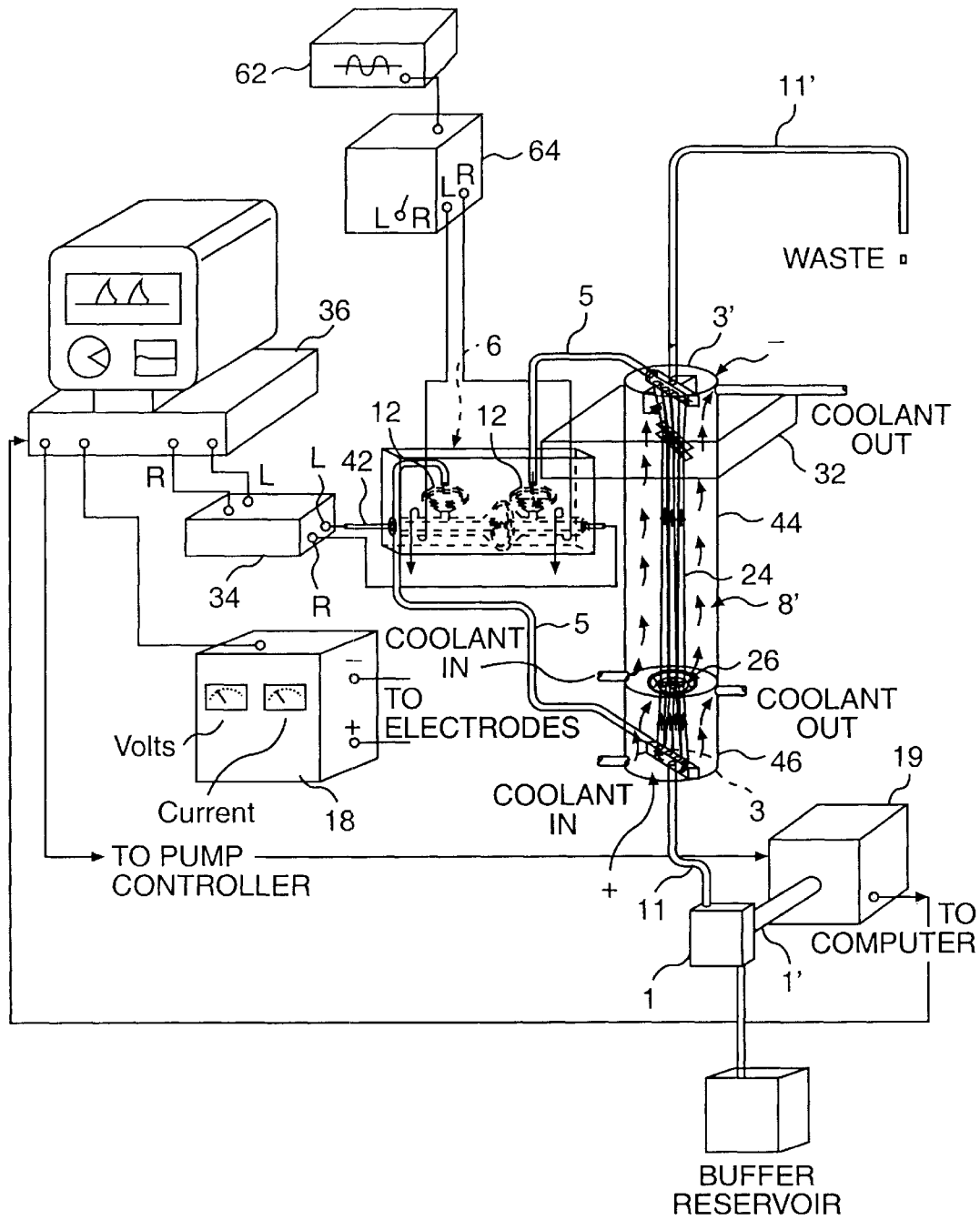
FIG. 4 shows the present invention as an analytic system.

FIGS. 3 and 4 show basic preparative and analytic CFFE systems, respectively, according to the present invention. For the preparative application, as shown in FIG. 3, buffer leaves a buffer pump 1 at a precise rate and enters an injector 2. A sample is injected through the injector 2 and is transported to a transition region 3 by fluid flow through lines of narrow bore HPLC tubing 11. In the preferred embodiment, in transition region 3, sample flow is conditioned to enter a separation chamber of multiple capillaries, 8 with minimum zone broadening. Alternatively, individual capillaries (not shown) may be used in place of multiple capillaries. Upper and lower bypass lines 5 of large bore Teflon connect the transition region 3 to a flow transducer 6. The flow transducer 6 is filled with mineral oil which is kept separated from buffer in the communication lines 5 by thin rubber containment diaphragms 12 (see FIG. 9).

Figure 5:
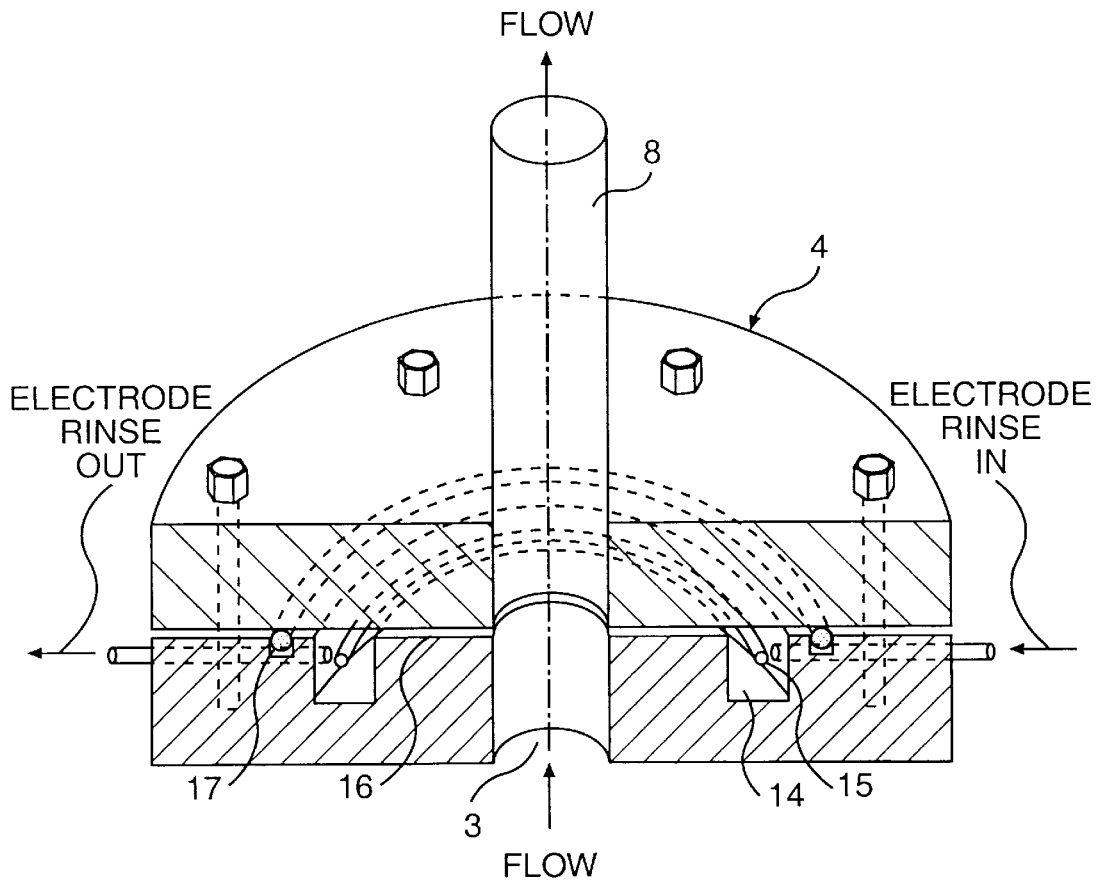
FIG. 5 shows the details of the connection between the electrode chambers and the separation chamber.

FIG. 5 details electrical communication between an electrode chamber 14 containing an electrode 15 and the separation chamber 8. This communication is provided by a conductive joint assembly 4 at lower and upper transition regions 3, 3' of the separation chamber 8. A piece of semipermeable membrane 16 runs between the separation chamber 8 and the electrode chamber 14. A constant flow of buffer renews the buffer in the electrode chamber 14. An O-ring 17 prevents leakage of buffer from the buffer joint assembly 4.

A band of inject sample (sample zone) enters the separation chamber 8 (multiple array of capillaries) and is separated under the action of the electric field as it moves with plug flow through the individual capillaries that make up the separation chamber 8. The flow transducer 6 senses very small pressure differences across the chamber and neutralizes these pressure differences through computer control of the electric field by means of a controlled power supply 18, thereby controlling electroosmotic and PDFs to achieve minimum sample dispersion within the separation chamber 8. Alternatively, the control could be asserted by altering the rate of the precision pump or by controlling both the buffer pump 1 and the power supply 18.

The electrophoretically separated sample exits the separation chamber 8 and converges in an upper transition region 3' into an exit line 22 and then moves into a detector cell 7. The exit lines 22 are short and small in internal diameter to minimize pressure-flow dispersion. From the detector cell 7 the separated sample enters a sample collector 13 and is processed in the same manner as separated samples in HPLC.

Figure 6:
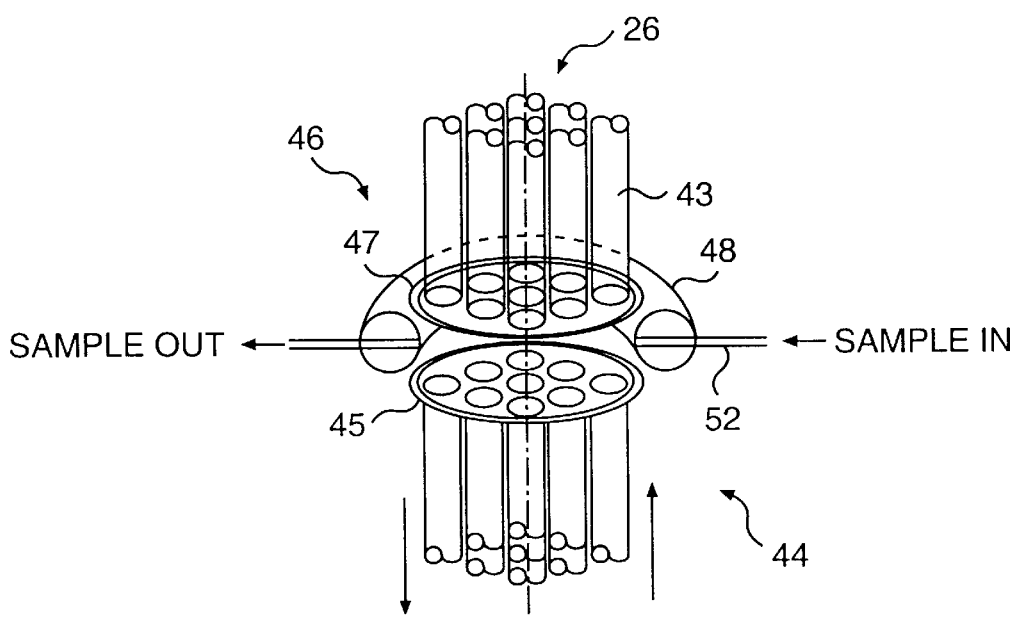
FIG. 6 shows an analytical multitube injector of the present invention.

FIG 4 shows an analytical version of CFFE, in which buffer passes through thin line 11 and directly enters the lower transition section 3 in the entrance chamber 8', directly from the buffer pump 1. The buffer flow is distributed to a separation tube, which in the preferred embodiment comprises an array of capillaries 24, by the transition section 3. Sample is injected using a novel on-line multitube injector 26 (see FIG. 6). Separation occurs in the tube array 24 located in the separation chamber and detection is accomplished by simultaneously passing a light beam through the tube array 24 in a detector 32 (see FIG. 7). From this point the buffer exits through an upper transition section 3' with the collection of the separated sample fractions being optional. The analytical separation chamber 8' is shown in greater detail in FIG. 8.

Buffer Pump

A common laboratory syringe pump can be used as the buffer pump 1; however, much better syringe pumps are available such as the CMA/100 microinjection pump made in Sweden. Alternatively, a peristaltic pump or HPLC-type pump can be used. Since the buffer at the pump is at high voltage, care must be taken that no leakage of fluid occurs. The high voltage is a hazard both for personnel and for the computer 36 and control circuits. One possible solution is to place the entire computer control and pump 1 within a protective enclosure to keep it isolated. Alternatively, as shown in FIGS. 3 and 4, the pump head (shown as 1 in the figures) could be driven by an insulating shaft 1' which would protect a pump drive and controller 19 and connected computer 36 from high voltage damage. The reproducibility of the system is directly dependent on the accuracy of the pump. An Ismatec 12-roller peristaltic pump head can deliver accurate flow rates down to 0.005 ml/min and hence would be satisfactory. Most of the other available pumps which could be used have reproducibilities of only about ±0.2%.

Sample Injector

The preparative sample injector currently used is a Rheodyne Model 7125 syringe-loading sample injector. Since the injector is made of stainless steel, it must be used outside of contact with the electric field; however, the injector body must remain at high voltage so a well-insulated actuation handle or servo-mechanism must be employed. An injector made completely of an insulating material such as Teflon® or machinable ceramic is preferable. The injector could then be placed entirely within the field immediately before the chamber inlet. This configuration would preclude any disturbance to the sampled zone that is possible in the lower pressure connection shown in the figures.

For the analytical version of the present invention, a custom in-line injector is used. This unique injector is characterized by a split-column design, illustrated in detail in FIG. 6, which shows that injection takes place between the lower entrance chamber 44 and upper 46 separation chamber sections. The lower 45 and upper 47 injector faces are lapped flat and made of thermally conducting ceramic cement with capillaries 43 embedded as shown. The faces are indexed so that they fit together aligned with each capillary 43 and with no dead volume. The composite column is sealed by an injector O-ring 48 through which the injection is made.

To inject, the lower section 45 is lowered so that a gap of approximately 50 $\mu$m exists between the faces 45, 47. Injection needles 52 are moved to penetrate the O-ring 48 and sample is pumped in to fill the gap between the faces 45, 47. Sample flows in through one needle 52 and overflow sample exits through the second needle 52' as indicated by the arrows in the figure. The injection needles 52 are then retracted enough so that compression of the O-ring 48 seals the needle holes. The faces 45, 47 are then brought together by moving the lower section 44 up as indicated by the arrow. The sample partly fills the capillaries which leaves a narrow zone of sample in each of the capillaries. The capillaries are now together with no dead volume. The buffer flow pump is then activated, power is supplied to the electrodes, and separation begins.

Flow Transition Regions

The lower flow transition regions 3 distribute the buffer flow to and collect the buffer flow from the separation chamber 8 in the preparative system or 8' in the analytical system (column tube array). Also, in the lower flow transition region 3 the flow changes from PDF at the inlet line to plug flow within the separation chamber 8 or 8' and back to PDF in the thin separation chamber exit line 11'. The two flow transition regions 3, 3' condition the flow from the inlet 11 to the separation chamber 8 or 8' and from the separation chamber 8 or 8' to the outlet 11'.

Electrode Chamber

It is important to ensure that the electrical communication joint 4 provides a rigid and leak-proof joint to electrically connect the electrode 15 in the electrode chamber 14 to the separation chamber 8. We have used dialysis membrane made of regenerated cellulose in the form of a gasket to effectively satisfy these requirements. In tests, the illustrated configuration has held a column of water 1 m high to less than 1-mm loss in 24 hours while exhibiting adequate conductivity. A schematic of the joint is given in FIG. 5. The electrode chamber 14 is adjacent to the separation chamber 8 to provide ample membrane area for the electrical current despite the thinness of the membrane 16 (about 75 $\mu$m per double thickness). To achieve lower voltage drops across the membrane, multiple layers can be used to produce a buffer joint with a larger effective conductive volume. Adequate clamping pressure on the membrane 16 precludes appreciable leakage and can be reproduced by using a torque driver on a bolt circle. Historically, other membrane configurations have been used in joints, but clamping the membrane 16 in the direction of the electrical current flow is the essence of this configuration and gives it rigidity that previous configurations have not provided. The rigid electrical buffer joint 4 is a necessary requirement for the CFFE concept because even minute movements of the electrical joint would cause pressure variations in the separation chamber which could not be compensated by the pressure transducer. That is, by ensuring that all components are rigid, detected pressure differences are certain to be caused by electroosmotic/pressure flow imbalances.

Separation Chamber

For analytical CFFE, a cylindrical capillary is the best choice because the flow is symmetrical about the center line and hence more uniform than square or rectangular capillaries which generate dispersion from flow in the corners. A column size of between 75- and 150-$\mu$m inner diameter will provide the physical size necessary to facilitate implementation of more efficient and precise injection and detection techniques. Multiple cylindrical capabilities are used in order to alleviate stringent detector requirements. About five tubes of 75-$\mu$m diameter would be sufficient.

As explained above, it is necessary to build the composite column in two sections. The lower section of 44 is the preinjection section which transitions the flow from a single inlet to the multiple capillaries 44, 43. The upper section of 46 is the separation and detection section. The injection takes place at the junction of these two sections. This novel configuration creates no dead volume, eliminates surplus sample from bleeding into the separation chamber, and wastes very little sample. The injector is similar to the breach mechanism used to load firearms.

Figure 7:
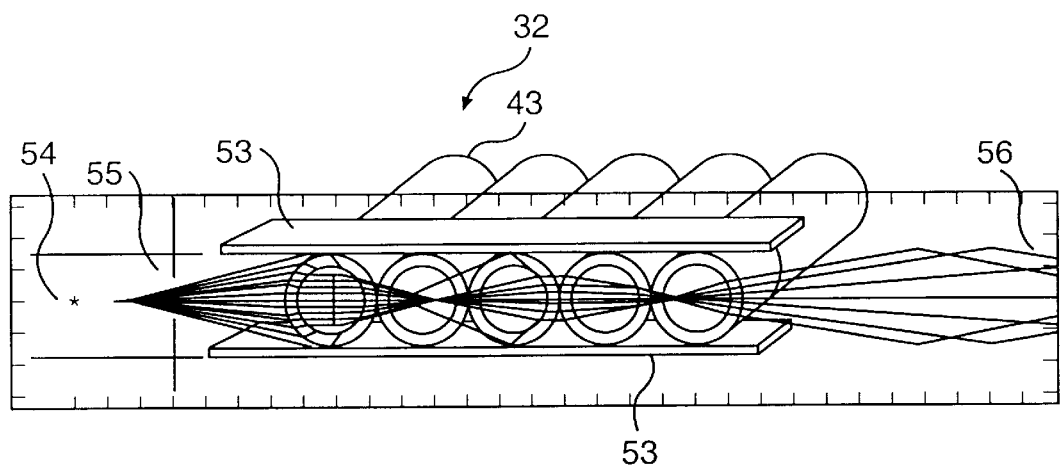
FIG. 7 shows an optical path of a detector used with the multitube array of the present invention.

At a position near the end of the capillary bundle, close to the upper transition region, the tubes are aligned side by side on an Invar base between two narrow blackened surfaces as shown in FIG. 7. Light from a UV source 54 passes through a slit 55 and follows a path through capillary 43 sequentially and at a right angle to each tube. Since the capillaries are round, light is deflected from a straight path through all of the tubes. But as the ray trace in FIG. 7 shows, about one-half of the light from a point source travels through the in-line capillary array to reach a photodetector 56. Thirteen typical rays enter the first tube. Four rays are trapped in the first tube by internal reflection, while two rays are trapped in the third tube. So the multiple tube arrangement is responsible for only about 15% of the loss since the first tube is essential. Therefore, the benefits gained by the longer path length outweigh the light loss in the multitube configuration. This results in a light path length equal to the combined diameters of the tube array and hence improves detector sensitivity greatly. The capillary surfaces not directly in the light path are painted black to absorb spurious reflections and hence limit the decoded sample absorption to the narrow zone defined by the entrance light slit.

Figure 8:
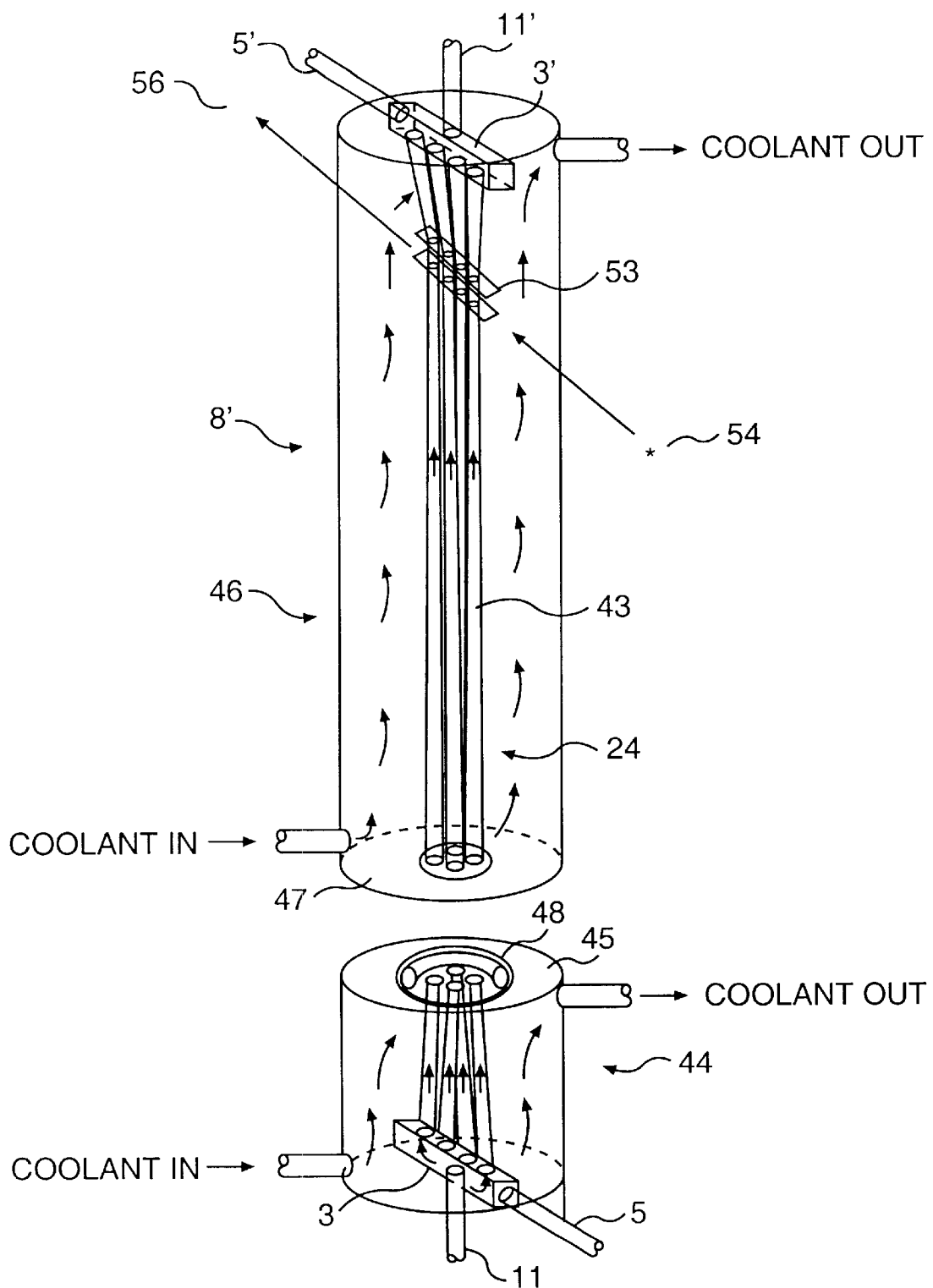
FIG. 8 shows a detailed view of the separation chamber of the analytical embodiment of the present invention.

FIG. 8 shows the CFFE analytical composite column 8'. Only four tubes are shown for clarity; also the spacing between the upper and lower sections is exaggerated for clarity. Electrode chambers similar to that shown in FIG. 5 would be situated at each end of column 8' to provide the electric field in the capillary tube array 24. Again the electrode chamber 14 are not shown nor is the mechanism for raising and lowering the lower chamber 44 for injection. During the separation process the sections are together with no space between them and sealed against external leakage by the O-ring 48 shown. The complete system would also have an external sample injector or auto sampler to supply samples in sequence to the in-line injector.

The system is cooled and kept at a preset temperature throughout the run by coolant flowing past the capillary tubes 43. The upper and lower chambers 44, 46 are cooled separately as shown. To assure that an unfavorable temperature gradient does not develop at the injector interface, the lower chamber 44 could be kept a few degrees cooler than the upper chamber 46. In the region of the injector and detector 56, copper paint or plating on the outer surfaces of the capillaries 43 could be used to further guard against adverse temperature gradients. The capillary tubes 43 extending from the injector to the detector 56 (upper chamber 46) must all be the same length and routed so that no "hot spots" occur, i.e., the coolant flow must be uniform around all the capillary tubes 43.

The initialization or preinjection is run with the gap set between the upper 47 and lower 45 injection faces. After the residual has stabilized and the column is ready for injection, the flow and voltage are discontinued. The sample is injected into the gap between the upper and lower chambers 46, 44, then the sections are brought together to form a continuous capillary array 24 from end to end. The flow and voltage are reapplied and the separation is initiated.

For preparative CFFE, capillary bundles 8 in the form of cylindrical and rectangular configurations preferably constitute the separation chambers. For a more detailed discussion of the dimensions and accompanying calculations, see the Alternative Preparative Embodiments section.

Flow Transducer

The flow transducer 6 is the heart of the CFFE system (see FIGS. 9, 10, 11, and 12 for details). For columns with diameters greater than 50 $\mu$m, precise control of the pressure across the column is necessary to achieve plug flow and avoid the sample dispersion that has plagued prior free-electrophoresis apparatuses.

Figure 12:
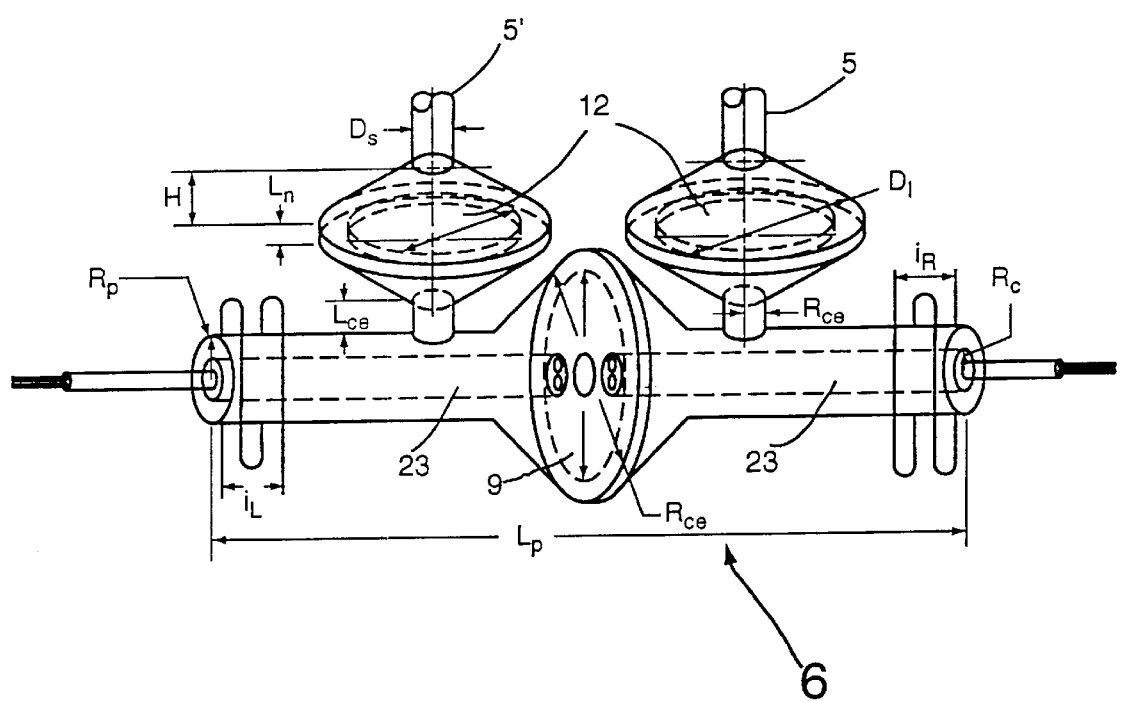
FIG. 12 shows a detailed diagram of the flow transducer of the present invention.

The cavities of the flow transducer 6 are filled with mineral oil to prevent electrical current in the bypass circuit (i.e., from the lower transition region 3 to the upper transition region 3'). Rubber containment diaphragms 12 confine the oil to the transducer 6. Two thin (150-$\mu$m-thick) rubber diaphragms 12 mounted on stainless steel rings and contained in conical transition chambers separate the conductive buffer in the bypass tubes from oil in the main bore of the transducer. Conical transition regions are positioned on each side of the diaphragms as shown in FIG. 12. Note that the conical region above the diaphragm is filled with buffer while the lower region is filled with oil.

The actual flow sensor consists of a thin rubber diaphragm 9 with two small reflective magnetic disks 17 on opposite sides at its center. The magnetic disks 17 are advantageously produced from a polished magnetic material or are coated with a reflective metallic layer or equipped with some other type of optical reflector. The diaphragm 9 is forced to move between two stops 25 (each of which comprises an end of an iron core 23) by an alternating magnetic field set up by two solenoids 22. Two optic fibers 42 are located in each stop; one fiber 42' brings in light from a source and the other fiber 42 transmits it back to a detector located in a signal conversion box 34. The signal converter 34, attached to optical fibers 42, converts optical signal from the flow transducer 6 to a digital signal which is fed into a digital comparator 36 (a PC). The computer 36 analyzes this signal and computes a DC-controlling voltage level, ranging between 0 and 10 V, for the power supply 12 and the buffer pump 1. The output voltage level from the power supply drives the electrophoresis and, together with the pump 1, produces plug flow in the separation chamber 8. When the diaphragm 9 is not contacting one of the stops 25, the reflective disk 17 transmits light between the fibers, and when the diaphragm 9 is on one of the stops 25, light transmission is blocked. The time spent on each stop 25 is indicative of the pressure across the separation chamber 8, and can be measured by a digital scan of the detectors. The difference of time on the right stop versus the left stop (i.e., pressure differences across the separation chamber) is the parameter upon which flow control of the entire system is based.

The flow transducer 6 responds to pressure across the ends of the separation chamber 8 as detected through wide bore (2.3 mm) Teflon™ bypass tubes 5, 5'. The wide bore is necessary to preclude frictional pressure drops in the connecting lines from influencing the operation of the flow transducer 6. The upper 5 and lower 5' flow transducer connecting tubes form a bypass between the separation chamber ends and communicate the pressure differential (across the column) to the flow transducer 6. The physics of the flow transducer operation were extensively analyzed during the design of the present invention.

Pressure difference across the column is measured in terms of a time difference reflecting the dwell of the diaphragm 9 against a respective stop 25, 25'. The time difference is determined by light transmitted or blocked at each respective stop 25, 25'. Light is transmitted by two optic fibers 42 from a light source to the ends of the iron cores 23. The light is then returned to a pair of detectors through two other optic fibers 42'. The ends of the iron cores 23 where the optics fibers terminate form seats against which the diaphragm 9 oscillates. Thus, light is alternately transmitted or blocked by the oscillating sensor diaphragm 9. The computer 36 digitally inputs samples at about 15,000 times a second. A light level near zero (darkness) produces a one while a level above zero (light) produces a zero. The times on a stop is then determined by the sum of the counts, i.e., ones. If there is no pressure difference across the flow transducer 6, the residence time of the diaphragm 9 on one stop versus the other will be the same. The pressure difference then reflects the sum of the counts over an arbitrary time interval.

The diaphragm oscillation is controlled by a function generator 62 which impresses a sine wave on the input of a dual-channel power amplifier 64. The amplifier has a balance control to vary the output to each channel. The power outputs is connected to the dual solenoids 22 of the flow transducer 6 so that the sensor diaphragm 9 is deflected magnetically from one stop 25 to the other 25'. If there is no pressure difference across the flow transducer 6, the residence time (i.e., the count) of the diaphragm 9 on one stop 25 versus the other 25' will exactly mirror the balance of the amplifier channels. Deviations from this balance represent pressure across the flow transducer 6. The preferred design uses an optical arrangement to detect the position of the diaphragm membrane 9 although other optical configurations and nonoptical detection methods are readily applicable without altering the essence of the design.

Sample Detector

The preferred detector for the preparative system is currently a Rainin Dynamat UVF filter UV detector with a microcolumn flow cell. This system is preferred because the flow cell and detector can be placed at the column fluid exit. The preparative CFFE system can readily use HPLC detectors and does not require custom on-line detectors; however, the analytical version of CFFE would require a custom detector. This detector would consist of multiple separation tubes aligned side by side to increase the effective detector path length. Normally a UV lamp source would be sufficient; however, for the highest resolution, a laser light source could be used. Also, some commercial models such as the Rainin Dynamat, OSC0 UA-5, or spectrum UV detectors could be used in less exacting roles. The CFFE column would replace the flow cells usually inserted in these detector configurations (see FIG. 8).

Computer

The computer 36 controls the separation process by manipulating the voltage output of the power supply in such a way as to minimize dispersion in the separation chamber. Currently, and lone ACL-711D multipurpose data acquisition card is used. The computer control is accomplished by the following steps:

1. The computer receives the digital input from the detectors in the form of a right count and a left count over a count period at a rate of, for example, 15,600 counts per second under the present configuration. The subtracted total of the counts is termed the residual.
2. The residual is kept to a preset value (usually zero) by the use of an algorithm based on the value of the residual and its time rate of change.
3. The algorithm determines the corrected voltage value, i.e., a control voltage from 0 to 10 V, and sends it to the power supply through an analog output.
4. The accumulated residual is analyzed throughout the run and if the residual value goes out of bounds the run is terminated by the computer.
5. The display on the monitor shows current residual, accumulated residual, time, and the output of the detector. The output of the power supply is shown both numerically and graphically on the screen.

The computer 36 balances the pressure across the flow transducer 6 by adjusting the power supply 18 to change the rate of electroosmosis in the separation chamber 8. The power supply 18 must be capable of producing a high voltage output and be computer controlled by signal from the computer 36 (in this case, an analog voltage).

Mode of Operation

CFFE is carried out in vertically oriented columns which may generally be of a larger bore than that used in CZE. A pump is used to ensure a precise flow rate through the column rather than depending on EOF to pump the liquid, as is done in CZE. Since there is now no dependence on wall conditions to control the flow of the buffer, reproducibility is greatly enhanced. Dispersion in the CFFE column is controlled by the pressure sensor which determines the ratio of pressure-driven to electroosmotically driven flow and controls it to maximize separation efficiency. Excess applied pressure will bias the alternating diaphragm in one direction, thereby resulting in an excess of counts, while excess EOF will bias the diaphragm in the opposite direction. Thus, CFFE is the first electrophoretic separation system where flow is controlled during the separation process.

We will look at a composite column since CFFE lends itself to the multitube configuration. This configuration can be used for both analytical and preparative separations and is amenable to scale-up. The fluid system shown in FIG. 9 consists of the separation chamber composed of a column bundle of $N_t$ tubes. The column bundle has an arbitrary rectangular shape with interstices between the individual tubes for coolant flow. The electric field E gives rise to an electroosmotic velocity $V_w$ at each tube wall in the direction of the PDF input, Q. The fluid system is induced to oscillate by a forcing function which is developed by impressing a sine wave perturbation on the sensor diaphragm 9. The forcing function is resisted by viscous forces and fluid inertia in the entire fluid system, and also by the two containment rubber diaphragms 12 in the flow transducer 6. Since the fluid may be considered incompressible, the flow rate is constant throughout the total fluid system. The velocities vary with the respective cross sections of the system components; in the analysis, all velocities will be referenced to the velocity of the sensor diaphragm center z.

We will now define a mathematical model which relates the pressure difference across the separation chamber to the response of the flow sensor. The pressure gradient in each tube is given by $$\frac{dp}{dx} = \eta \frac{1}{y} \frac{d}{dy}\left(y \frac{du}{dy}\right)$$

where
p=the pressure in the chamber
$\eta$=absolute viscosity of the buffer,
x=axial coordinate,
y=radial coordinate, and
u=axial fluid velocity in the chamber Solving this equation gives the velocity distribution across an individual tube cross section, $$u = \frac{1}{4\eta} \frac{dp}{dx}(y^2 - a^2) + V_w \quad (7)$$

where $V_w = \mu_w E$.

$\mu_w$ is the fluid mobility at the wall and E is the impressed electric field.

The flow in one capillary is $$Q_i = -\frac{\pi}{8\eta} \frac{dp}{dx} a^4 + \pi a^2 V_w$$

so that the pressure drop is given by $$\frac{dp}{dx} = \frac{8}{\pi} \frac{\eta}{a^4} (\pi a^2 V_w - Q_i) \quad (8)$$

where $Q_i$ is the flow in one capillary, and dp/dx is the pressure gradient in any capillary. The above expression was derived for an open capillary by Roberts[19].

Then the pressure in the chamber depends on a balance between the EOF in the chamber and the PDF entering the chamber.

It can be seen in equations (7) and (8) there exists a voltage gradient (E=$E_n$) which will produce plug flow dp/dx=0 in each capillary, i.e., when the total flow Q is $Q_i = \pi a^2 \mu_w E_n$ and $Q = N_i Q_i$ where $\mu_w$ is electroosmotic wall mobility, and $E_n$ is the (unknown) null voltage gradient. Here we have made use of the expression $V_w (= \mu_w E)$ to express plug flow in the chamber. Then using equation (8) we have $$\frac{dp}{dx} = \left(\frac{8\eta\mu_w}{a^2}\right)(E - E_n). \quad (9)$$

A negative pressure gradient dp/dx produces a positive directed flow and is present when $E_n > E$; while a positive pressure gradient produces a negative flow and is present when $E_n < E$.

Therefore, we see that the pressure gradient and the accompanying pressure-driven dispersion can be controlled by the applied voltage gradient in a CFFE configuration.

In order to appreciate the level of accuracy required in utilizing this pressure control method, we make an estimate by neglecting the mitigating effect of diffusion. The pressure difference across the column $\delta p$ distorts the plug flow (EOF) profile so that a particle in time, $\tau$, travels $\delta l$ further at the center line[14] than a similar particle travels at the wall. This parameter $\delta l$ is defined as the displacement and characterizes the parabolic displacement profile in open tubes in the absence of lateral diffusion after an interval of time. In this case, the time is the residence time for the separation $$\delta l = u_o \tau \text{ and } \tau = \frac{L_c}{\mu_w E}$$

but $$u_o = -\frac{a^2}{4\eta} \frac{\delta p}{L_c}$$

where $\delta p$ is the pressure drop across the column length $L_c$. Then the pressure difference responsible for the displacement $\delta l$ is given by $$\delta p = -\frac{4\delta l \eta E \mu_w}{a^2}.$$

Consider the allowable pressure difference across a column under the following conditions: $\alpha$=0.00375 cm, $\mu_w$=0.00051 cm$^2$/V sec, E=200 V/cm, $\delta l$=0.10 cm, then $\delta p$=2.8×10$^{-2}$ cm of water. This again confirms the sensitivity of capillary electrophoresis due to small pressure differences when the smoothing effect of molecular diffusion is not present.

This tiny pressure is not readily measured; indeed, only the most sophisticated and expensive of pressure transducers could measure a pressure of this magnitude. Even then, these transducers can measure only dry air as they are capacitive in nature. Any practical pressure sensor would not respond to pressure differences of this magnitude. The solution to this dilemma is to perturb the fluid system at pressures many times greater than the pressure being measured. The perturbations exercise the system to produce a measurable result which then indicates the true pressure difference sufficiently to control the separation.

Figure 9:
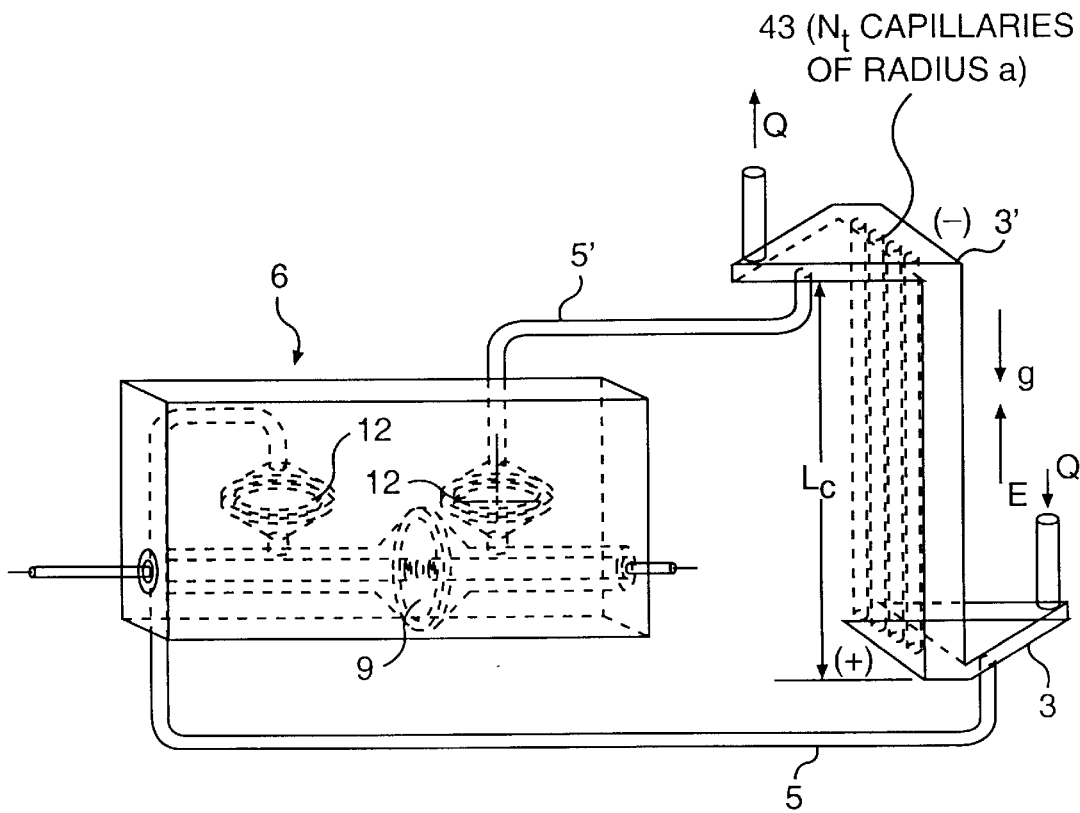
FIG. 9 shows details of the flow transducer connected to one embodiment of the separation chamber of the present invention.
Figure 10:
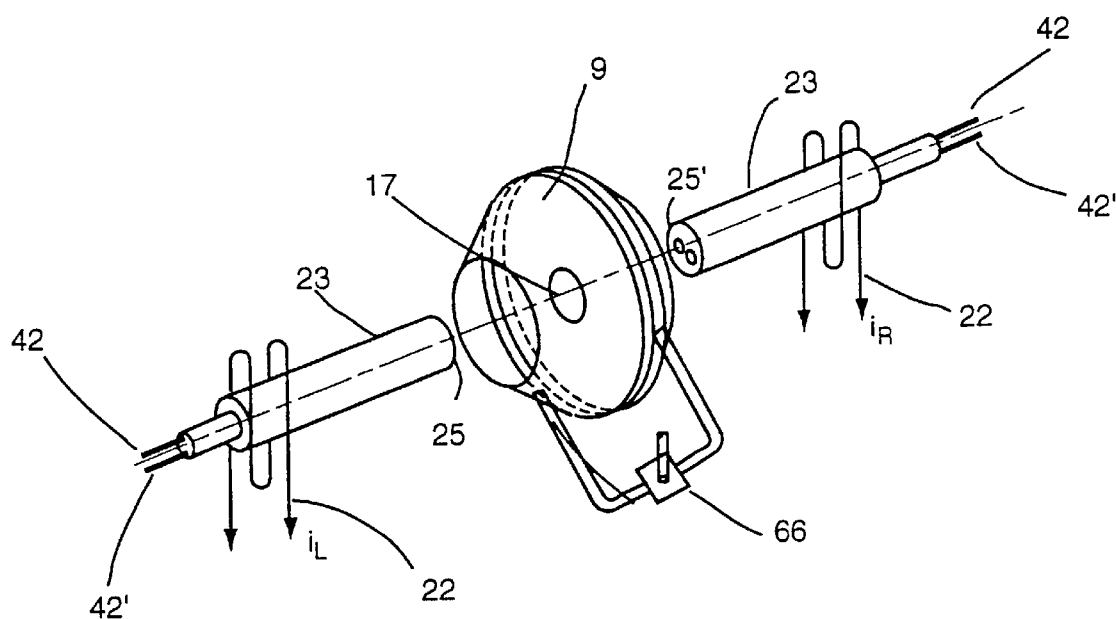
FIG. 10 shows a detailed view of the flow transducer of the present invention.
Figure 11:
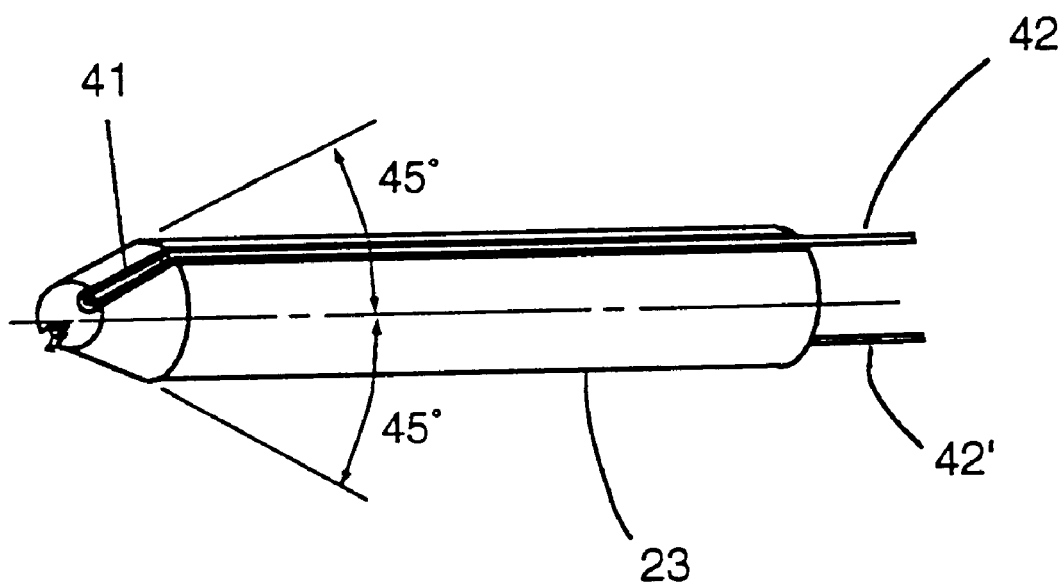
FIG. 11 shows a detailed view of an iron core of the flow transducer of FIG. 10.

Consider the system shown in FIG. 9 and the flow transducer detail shown in FIG. 10. Two small magnetic disks 17 with reflecting metallic cover plates are attached to each side of the sensor diaphragm 9, and this entire assembly moves between two stops 25. Note that the end of the extended iron core 23 of the solenoid coil 22 serves as the diaphragm stop 25. Two fiber optic conduit grooves 41 containing two fibers pass along the periphery of each iron core as shown in the iron core detail in FIG. 11. Note that the fiber ends are at an angle of 90 degrees to each other. The solenoids 22 can be energized to cause the diaphragm 9 to execute sinusoidal motion. The time on each stop 25 can be determined by a digital scan of detectors and hence produce a count. The solenoids 22 are energized in parallel using the sinusoidal output of a function generator 62. By controlling the electric current in each parallel circuit (with a balance control), the center of oscillation can be varied. This allows for the zero calibration of the fluid system prior to a run.

With the system static, a bypass valve 66 is opened to equilibrate the pressure across the sensor diaphragm 9. After closing the equilibration valve 66, the static fluid system is excited by energizing the solenoids 22. The current to each solenoid 22 is adjusted to produce a zero count or residual by the computer 36. This is the calibration condition of zero pressure difference across the separation chamber 8 and hence defines this condition during the separation process. The buffer pump 1 and electrophoresis power supply 18 are then actuated. The condition of zero residual can then be recovered by adjusting the power supply voltage under computer control.

There exists, as previously described, a chamber voltage which will produce a purely EOF in the chamber, i.e., plug flow. This condition is given by $$Q = N_t Q_t = N_t \pi \alpha^2 \mu_w E_n.$$

This voltage gradient $E_n$ is a function of the input flow rate Q and is termed the null voltage gradient. The pressure difference across the chamber ends is $$\delta p = \left[\frac{8\eta \mu w}{a^2}\right](E - E_n)L_c.$$

If the sensor excitation is sinusoidal, the forcing function on the sensor diaphragm is given by $$\delta F = \delta f \sin(\omega t)$$

where $\delta f$=amplitude of the magnetic-induced perturbation, $\omega$=perturbation angular velocity, and t=time.

The force, $\delta f$, will depend on the number of turns of wire in the solenoid coils 22, the electric current in the coils 22, and the magnetic permittivity and shape of the iron core 23. The force, $\delta f$, must be strong enough to oscillate the fluid system so that the diaphragm engages both stops during its motion. The sensor is caused to move by the oscillation of the magnetic actuator and its center plane of motion is determined by the pressure difference across the separation chamber ends.

The total force on the sensor diaphragm 9, F(t), equals the force due to $\delta p$ across the separation chamber plus force produced by the sensor excitation plus the fluid force $$F(t) = -\pi D_s^2 \delta p + \delta F + f_d + f_s \qquad (10)$$

$$F(t) = -2\pi \eta \mu_w \left(\frac{D_s^2}{a^2}\right) L_c(E - E_n) + \delta f \sin(\omega t) + f_d + f_s$$

where $f_d$ is the force exerted on the diaphragm by the fluid system, $f_s$ is the tension developed by the diaphragm, $D_s$ is the sensor diaphragm diameter, and $\alpha$ is the radius of an individual tube.

As the diaphragm oscillates it must move the entire fluid system, resulting in a force $f_d$ on the diaphragm. The major force exerted on the diaphragm is from the fluid being forced to flow in the separation column tube array. For small oscillations the volume displaced by the oscillating sensor diaphragm is given by $$V = \frac{\pi}{8} D_s^2 z$$

where $D_s$ is the diaphragm diameter, and z is the diaphragm displacement about its center of motion.

The flow rate of fluid is then $$Q_d = \frac{\pi D_s^2}{8} \dot{z}.$$

Now consider the PDF (neglecting EOF) of fluid $Q_t$ in the $N_t$ tubes making up the separation column $$Q_t = \frac{N_t \pi}{8\eta}\left(\frac{d}{2}\right)^4 \frac{p_d}{L_c}$$

where d is the individual tube diameter and $p_d$ is the pressure on the diaphragm due to the imposed flow.

Noting that $$p_d = \frac{4}{\pi}\frac{f_d}{D_s^2}$$

we can write $$Q_t = \frac{N_t}{32\eta}\frac{d^4 f_d}{L_c D_s^2}.$$

Then the flow produced by the diaphragm movement must equal to the flow in the tubes, so $$Q_t = Q_d,$$

$$f_d = 4\pi \left(\frac{D_s}{d}\right)^4 \frac{\eta L_c}{N_t}\dot{z},$$

and $$f_d = F_v \dot{z},$$

where $$F_v = 4\pi \left(\frac{D_s}{d}\right)^4 \frac{\eta L_c}{N_t}$$

is the measure of tube resistance to flow produced by the diaphragm. Note the dependence of this resistive force on the fourth power of the diaphragm and tube diameters. The tension force developed by the diaphragms can be expressed as the sum of the initial tensions times the displacement.

The fluid in the system may be considered as a lumped mass approximation since the fluid is incompressible. Note the term (E−En) determines the direction of the force, if E>En, EOF dominates and gives rise to negative displacements of the center of oscillation. If E<En, PDF dominates and gives rise to positive displacements.

The equation of motion can be written using the above equations providing a solution consisting of both steady-state and transit terms. Note that there are two containment diaphragms and one sensor diaphragm.

Figure 13:
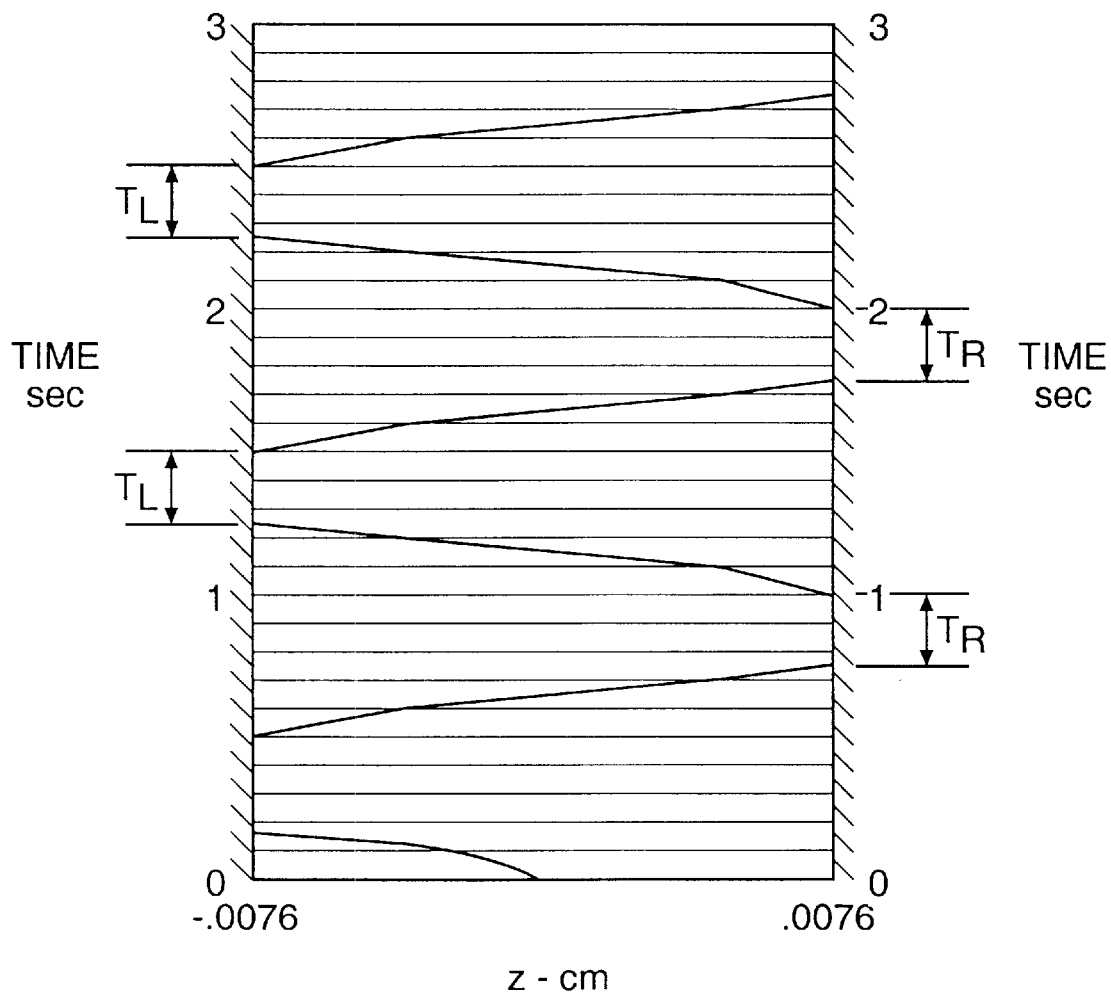
FIG. 13 shows a plot giving the relationship between flow transducer diaphragm position and pressure in a CFFE separation as defined by the parameters in the figure.

By referring to the flow system schematic (FIG. 9) and to the flow transducer detail (FIG. 10) we see that an excess of pump flow into the chamber will cause PDF in the chamber as indicated by la pressure difference across the diaphragm 9 which would cause it to remain on the right stop 25' longer than on the left stop 25 (i.e., $T_L<T_R$) in FIG. 13 when exercised by the magnetic force, which is large enough to cause oscillatory movement of the diaphragm 9. However, if the EOF is greater than the flow entering the chamber, a pressure gradient will be developed in the chamber to force fluid back toward the flow entrance. This pressure difference biases the diaphragm to spend more time on the left stop.

The residual (DT) can be determined for each cycle and the voltage gradient E adjusted in real time to minimize the accumulated residual over the course of the run. Also, since small PDF's can be used to correct for certain kinds of dispersions, the residual could be maintained at a preset value which would minimize these disturbances.

The equation of motion provides z(t) which can be used to determine when the diaphragm arrives at a respective stop, i.e., z=±δL. The time when the diaphragm leaves the stop will be determined by a change of sign of the forcing function, i.e., t=(2n−1)/ω for leaving z=+δL and t=2n/ω for leaving z=−δL.

Starting at the midpoint at t=0, the diaphragm moves to the right stop under the action of F(t) where it stays as long as the force is in the original direction. When the force changes direction the diaphragm moves to the other stop. Equations have been developed describing the precise motion of the diaphragm as it moves between the two stops.

There will be a certain amount of noise generated by the flow sensor. We define this noise as the output of the flow sensor (in counts) when the pressure differential is known to be zero. This is measured when the flow transducer is actuated (unconnected to the separation chamber) with atmospheric air pressure on both containment diaphragms.

During separation over a period of 15 to 30 minutes the count due to noise should average out, but during the run we may not distinguish noise from a meaningful signal. Therefore, we must measure all of the signal and apply the necessary corrections in real time. This requires that the power supply output be controlled to a high degree of resolution. We are currently using a digital analog voltage signal of 0 to 10 V DC with 12-bit resolution. This translates to increments of output voltage from the 20-kV power supply of 4.8828 V or a voltage gradient of 0.0488 V/cm for a 100-cm-long separation column. Depending on the noise generated by the flow sensor, this might not be accurate enough. If this is the case, 16-bit resolution could be used where the discernible voltage gradient would be 0.0061 V/cm.

It should be noted that the accumulated residual is kept at a minimum throughout the run and except for the instantaneous error caused by the sensor noise, δl should remain small. Some dispersion does occur from the nonzero instantaneous δl, but this dispersion will be compensated for later when noise of opposite sign and equal magnitude occurs. This is the reason for using the accumulated residual instead of the instantaneous residual to control the dispersion.

Advantages Over Prior Art Systems

In CFFE operation hydrodynamic flow dispersion is controlled by the flow transducer, while in CZE operation it is not controlled at all (i.e., it is not considered a significant problem). The literature devotes only a passing interest to the issue, statements like "The absence of hydrodynamic flow in the capillary is a very important condition for efficiency of capillary electroseparation methods"[3] are typical of one line of thought. Other references[10] mention hydrostatic flow as being important, but go into no detail. Others take a more lenient position concerning hydrodynamic flow. In a handbook on CZE[16] (in a footnote on troubleshooting), it is advised that the hydrodynamic head must be in a range of 5 cm of water to be an appreciable factor in narrow bore capillaries (i.e., <75 $\mu$m).

We will compare separation efficiencies for CZE and CFFE in terms of theoretical plates as defined by Giddings [7]. Assume that the nominal height between ends of a capillary is 10% of the handbook value given above. This assumption is reasonable since CZE practice does not include precise leveling techniques.

The effect of hydrodynamic flow dispersion on the separation efficiency in terms of number of theoretical plates N per length of capillary $L_c$ is given by the equation below $$\frac{N}{L_c} = \frac{393{,}216\eta^2 D_m \mu_w E}{g^2 \left(\frac{\delta h}{L_c}\right)^2 d_c^6}$$

where $D_m$=molecular diffusivity, cm$^2$/sec, $L_c$=capillary length, cm, $\mu_w$=wall mobility, 5.1×10$^{-4}$ cm$^2$/V sec, E=electric field, 200 V/cm, $d_c$=capillary diameter, cm, and δh=height difference between the tube ends, cm.

FIG. 17 shows results from the above equation in terms of separation efficiency $N/L_c$. The curves represent a value for $\delta h/L_c$ and are defined in alphabetical order from left to right. Note that the ratio $\delta h/L_c$ is really a measure of the mean pressure gradient causing the hydrodynamic flow disturbance. In general, the curves show that below a diameter of 100 $\mu$m the pressure gradient makes little difference in performance for materials of high diffusivity. The curves of $\delta h/L_c$ nearly overlap each other for small molecules in narrow bore capillaries. In particular for FIG. 17*b* (diffusivity of proteins), a column diameter of ~75 $\mu$m gives high performance for high values of $\delta h/L_c$; this is in agreement with CZE practice. As $D_m$ decreases, the pressure gradient becomes more important as a comparison of the graphs shows. This observation is in agreement with the literature and CZE practice. While CFFE would have its greatest advantage over CZE for larger molecules and particles, it would also be attractive for analytical and preparative separations of smaller molecules because of its chromatography format and ability to collect sample.

For small molecules and small capillaries, the handbook advice that hydrodynamic dispersion is of no concern, is reasonable; however, for large molecules, the hydrodynamic flow dispersion is significant. Obviously, with great care, a much greater accuracy than 0.5 cm could be achieved in leveling, but the uncertainty of the meniscus at the tube ends and the physical labor of maintaining equal reservoir surface levels would preclude any practical control of hydrodynamic dispersion in CZE operation.

In CFFE, however, control of hydrodynamic dispersion is a necessary condition for success. For small capillaries and small molecules there would not be a significant difference in performance between CZE and CFFE, but for larger capillaries and larger molecules, the performance of CFFE would be much better than CZE. Indeed, CZE is impractical for large bore capillaries, as FIG. 17 clearly shows.

To better compare the performance of CFFE to that of CZE, we need to separate the flow disturbance (i.e., the parabolic displacement of plug flow) from the mitigating effect of lateral diffusion[19]. Above, we defined the displacement δl as the relative movement of fluid at the center line relative to that at the tube wall during the residence time of the separation. The separation efficiency in plate numbers N can be expressed as $$N = \frac{384 L_c^3 D_m}{\delta l^2 V_w d_c^2} \quad (11)$$

and $$\delta l = \frac{g \Delta h d_c^2}{16 \eta V w}.$$

Consider the case for a 75μm capillary, where
  Δh=pressure differential—0.5 cm $H_2O$,
  $d_c$=capillary diameter—75 μm,
  $V_w$=EOF velocity—0.102 cm/sec,
  $D_m$=molecular diffusivity—1×10⁻⁶ cm²/sec, and
  η=fluid viscosity—0.01 gm/cm sec.
Combining these equations we find that N≈3×10⁶, which is quite large, but that δl=1.69 cm. If a sample with $D_m$=1×10⁻⁵ were used, the plate count would be about 3×10⁵. These are high values for separation efficiency despite the rather large value of displacement. Clearly CFFE would not have a great advantage (from an analytical separation standpoint) over CZE in terms of resolution for small molecules using small diameter capillaries. However in CFFE where small displacements (δl) can be maintained, the advantage would be more pronounced for larger molecules separated in larger capillaries.

In summary, CZE practice does not address the problem of hydrodynamic dispersion; however, the control of hydrodynamic dispersion is a necessary condition for the success of CFFE. The control of hydrodynamic dispersion will lead to higher separation efficiencies and is especially significant for large bore capillaries and/or larger sample molecules; i.e., proteins.

We suggest that analytical electrophoresis can be much improved by using multiple capillaries with simultaneous detection through the aligned bundle. In this configuration the detector path length will equal the combined internal diameters of the number of capillaries used. With ten tubes, for example, the detectable sample concentration could be reduced by an order of magnitude.

Injection of the sample is probably the weakest link in CZE practice. For analytical CFFE, sample injection is precise and reproducible. Larger sample volumes can be used which reduces fluid handling problems. The CFFE sample injection technique can produce very narrow sample injection zones without relying on stacking[22]. The CFFE injector surfaces can be accessed to allow thorough cleaning so that contamination between runs is precluded. In the case of preparative CFFE, standard LC injectors can be used, making CFFE an inexpensive augmentation to standard laboratory separation equipment.

Detection requirements for analytical CFFE are far less demanding than those for CZE because of the much longer detector light path lengths possible with the multitube configuration. With multitubes, the possibility of using commercial LC detectors is even possible in an on-line configuration. The longer path length also allows lower concentrations to be used in analytical determinations. In CZE, the short light path lengths produced by viewing across single capillaries of narrow bore dictates high sample concentrations. Again, in preparative CFFE, there exists the practicability of using commercial LC detectors in the usual chromatography configuration.

As mentioned, analytical CFFE is capable of detecting samples of low concentration. This is a great advantage in reducing electrokinetic dispersions[13]. Low sample concentration reduces zone broadening[17] and is indeed the assumption made for all electrokinetic calculations. Low concentration will also reduce solute adsorption on the capillary walls and hence further reduce zone broadening. The lower sample concentrations permit the use of lower buffer concentrations which, in turn, produce lower thermal dispersion and electrokinetic disturbances. In preparative CFFE, where high sample concentrations are required for high throughput, the multitube configuration consisting of narrow bore capillaries provides the necessary "wall effects" to reduce the disturbances produced by the high concentrations. The configuration also provides support for the sample against convective disturbances such as diffusion-driven instabilities.

Preparative CFFE will give much greater resolution than LC. Eddy migration greatly affects separation efficiency in LC on both a local and global scale[13]. In CFFE there is no local eddy migration since all samples travel the same path in each separate tube, while global eddy migration is controlled by varying the voltage and temperature fields. Preparative CFFE has the feature of practically unlimited scale-up. As the separation chamber is made larger in a cross-section area, additional cooling passages can be added to control the buffer temperature while programming the effective field strength and coolant flows to provide maximum separation efficiency.

In analytical CFFE on a local scale and also in preparative CFFE on a global scale, the flow can be manipulated through the flow transducer in terms of a nonzero residual to compensate for thermal distortion and stable convective flows.

Alternative Preparative Embodiments

Figure 14A:
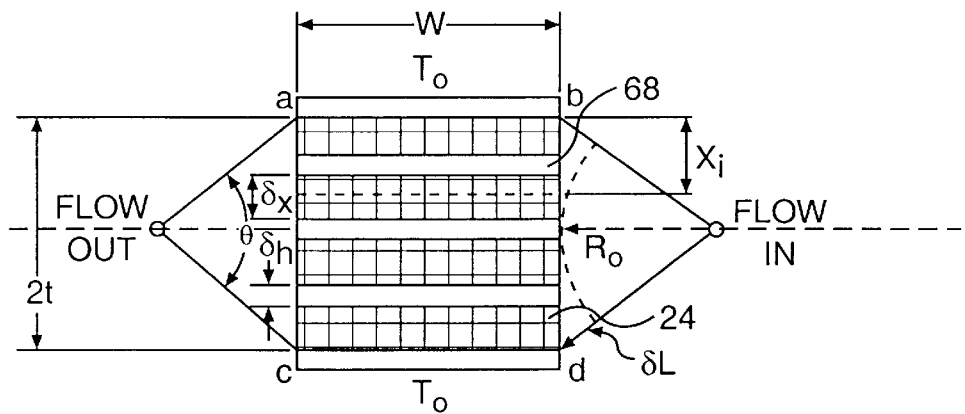
FIG. 14 illustrates an embodiment using a rectangular separation chamber comprised of a plurality of capillaries that are rectangular in cross section.
Figure 14B:
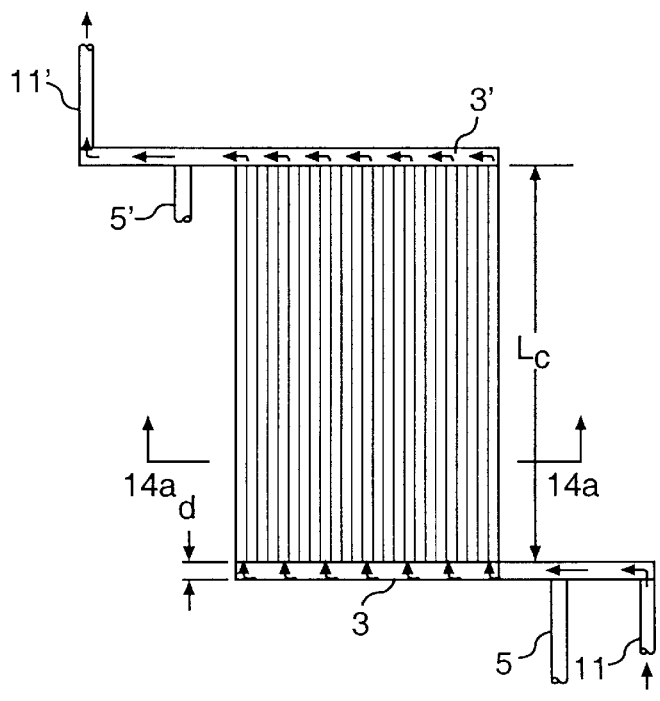
Figure 14C:
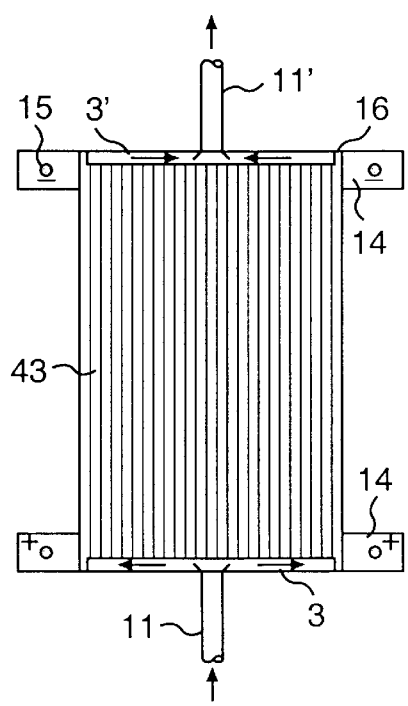
Figure 17B:
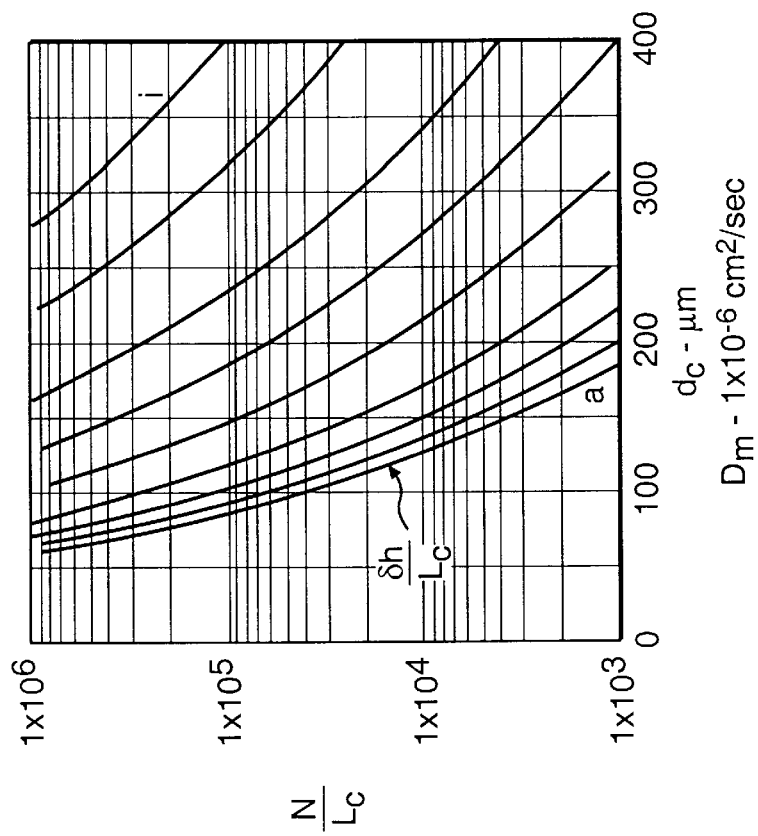
FIG. 17 shows the effect of dispersion on separation efficiency (plate number per unit length of capillary) using capillary tubes of different diameters in the present invention.
Figure 17A:
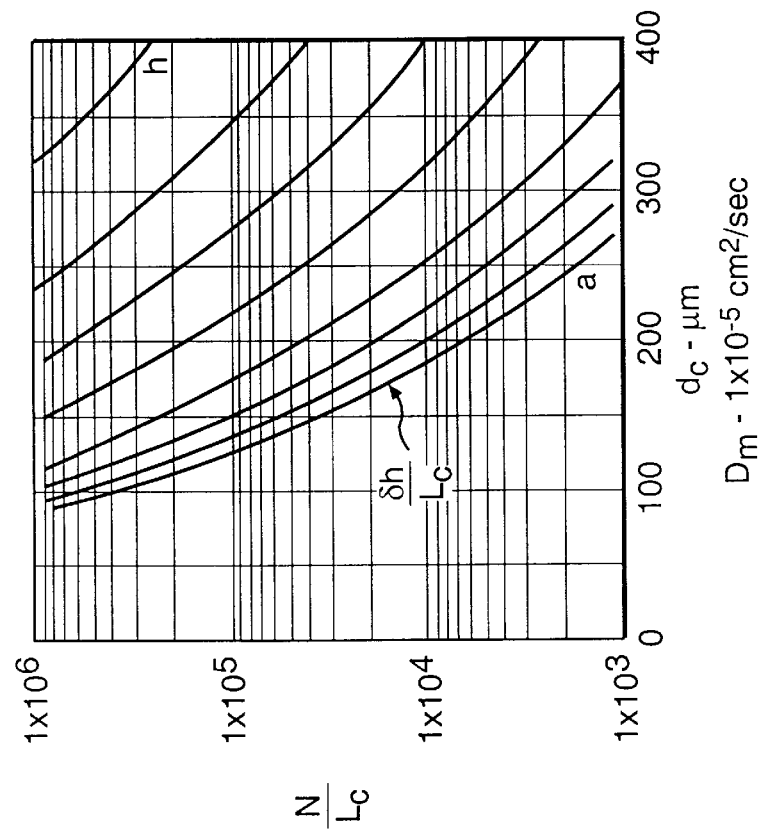
Figure 17D:
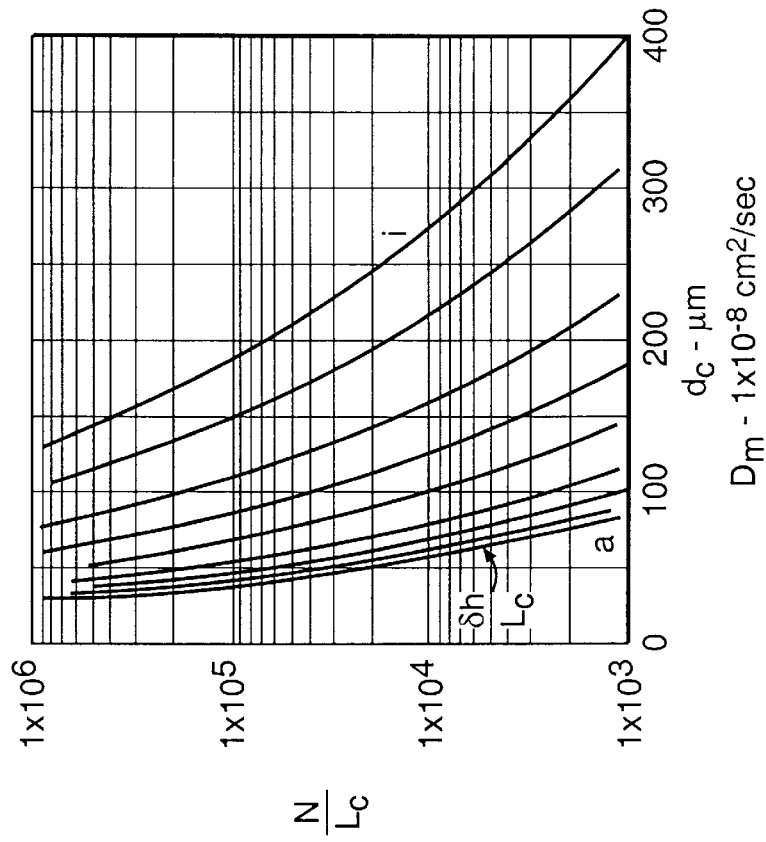
Figure 17C:
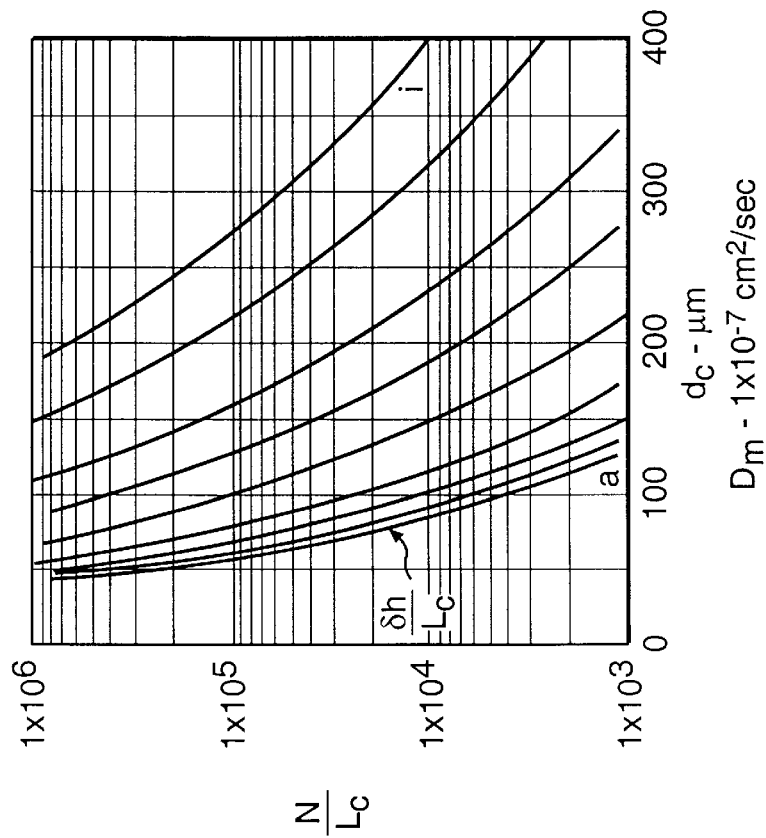

The design of any preparative device is made difficult by the necessity to apply uniform conditions over the active chamber cross section. In HPLC, this cannot be done, since it is impossible to control pressure over the chamber cross section. However, in CFFE we can manipulate the electrical and temperature fields to control the flow in such a way as to minimize dispersion over very large cross-sectional areas. This is of great importance since large cross sections produce large throughputs. Consider the square cross-section configuration comprised of multiple square capillary mini-section arrays shown in FIG. 14.

The carrier flow and sample zone enter the chamber 8 through the entry line 11 and flow through the transition chamber 3, expanding along an arc. This is seen most clearly in Section A—A where the wedge shape of the transition chambers 3, 3' are most apparent. Since the flow in the transition chambers 3 is radial, flow near the edges moves further than flow on the chamber center plane by the distance δL. This inequality of flow paths causes a slight dispersion which will be put into context later. The flow continues into the separation column and follows equal paths in planes parallel to the center plane. The flow then leaves the separation chamber 8 through the exit line 11' in the same manner that it entered the chamber.

In Section A—A, the multitube separation sections or arrays 24 are of width δx. These tube arrays 24 are separated by cooling channels 68 of width δh through which flows cooling water. The distance from the outside edge of the chamber to the center of each separation array is $$x_i = (i-1)(\delta h + \delta x) + \frac{\delta x}{2}, \quad 1 \le i \le N,$$

where N is the number of separation arrays on one side of the center plane, i.e., 2N arrays for this device. The number of capillary tubes 43 in each separation array is $$n(x_i) = \frac{(\delta x w)}{l_o^2}$$

where $l_o$ is the outside dimension of each tube.

The electric current enters the separation chamber 8 from four electrode chambers (two positive and two negative) along a-b and c-d as shown in the diagram. This manner of applying the electric field causes a nonuniform field in the column. The nonuniform voltage gradient developed in the separation column is $$E(x_i) = \frac{V_o}{L_c \left[1 + \frac{2x_i \delta x}{L_c d} \frac{l_i^2}{l_o^2}\right]}$$

where $l_I$ is the inside dimension of each tube.

This voltage field causes sample on the center plane to move more slowly than similar sample at the edges. In order to correct for this potential cause of dispersion we cool the chamber with 2N cooling channels 68 so that the temperature distribution is given by $$T(x_i) = T_o + \delta T(x_i)$$

where $T_o$ is the temperature on the outside walls. This will give a higher temperature at the center plane where the electric field is weakest. The sample velocity is then $$v(x_i) = (\mu_{wo} - \mu_e) E(x_i) [1 + 0.02 \delta T(x_i)]$$

where $\mu_{wo}$ is the electroosmotic wall mobility and $\mu_e$ is the sample fraction electrophoretic mobility on the outside edge where $T=T_o$. Combining equation we obtain $$v(x) = (\mu_{wo} - \mu_e) \frac{V_o}{L_c} \left[\frac{1}{1 + k x_i \delta x}\right][1 + 0.02 \delta T(x_i)]$$

where $$k = \frac{2}{L_c d} \left(\frac{l_I}{l_o}\right)^2.$$

The temperature difference $\delta T(x_i)$ is controlled by manipulating coolant flow in the chamber cooling passages, with the temperature field for exact compensation given by $$\delta T(x_i) = 50 i x_i \delta x \,°C,$$

where $\delta T(x_i)$ is the temperature difference between the edges (a-b and c-d) and the center plane. By maintaining $\delta T(x_i)$, an equal migration field will exist in the separation chamber and the above dispersion effects will be eliminated. The first origin of dispersion discussed, i.e., the unequal flow paths in the transition region is usually of very small consequence but it too can be controlled by modifying the voltage gradient $E(x_i)$ defined above by the proper choice of d.

Thus, the variation of the electric field is largely dependent on the thickness of the transition chamber d. A large value of d will reduce the variation. It would be possible to enlarge the thickness of the transition region and stabilize the flow with a stabilizing matrix, such as addition of small glass or other inert beads 72, in the transition region. EOF could cause a problem in the entrance 3 and exit 3' transition regions; if this is the case, the cooling channel area 68 could be coated to reduce or eliminate the EOF. Some sample attachment near the electrodes is also possible so that flow by the electrodes should be high enough to control this problem.

The foregoing example is but one configuration for preparative CFFE. A cylindrical composite column could also be used with the fluid entering and exiting at each end along the chamber center line. A schematic of this configuration is shown in FIG. 15. Here, as before, a nonuniform electric field exists, the field being weaker at the center line. Control of the flow in the annular passages 68 sets the radial temperature distribution. Thus, nonuniform voltage and temperature fields exist. These effects combine, as before, to eliminate distortion in the separation capillaries 43. The unequal paths for the sample can be greater than those in the previous example and are equal to the radius of the chamber 8. This source of dispersion can, however, be compensated for by reducing the EOF at the center region of the column by manipulation of the electric field through variation of the transition section thickness d.

The voltage gradient in the column is given by $$E(r_i) = \frac{V_o}{L_c} \left[\frac{1}{1 + \frac{2 k r_i}{\pi L_c d} \frac{(R_o - r_i)}{(R_o + r_i)}}\right]$$

where $d_i$=inside diameter of a capillary,
$d_o$=outside diameter of a capillary, $$k = \frac{\pi^2}{2} \delta \left(h\left(\frac{d_i}{d_o}\right)\right)^2,$$

and the radial distance to the center of the $i^{th}$ separation section is $$r_i = R_i + (i-1)(\delta h + \delta r) + \frac{\delta r}{2}.$$

Note that there are $n(r_i)$ tubes in each section, i.e., $$n(r_i) = 2\pi \frac{\delta h}{d_o^2} r_i.$$

The migration velocity is $$v(r_i) = (\mu_{wo} - \mu_e) E r_i [1 + 0.02 \delta T(r_i)]$$

where $\mu_{wo}$ is the wall mobility at the outside separation section where the temperature is $T_o$ and $\delta T(r_i)$ is the temperature variation from $T_o$ in the column interior.

For exact compensation, the temperature variation $\delta T(r_i)$ must be $$\delta T(r_i) = 100 \frac{kr_i(R_o - r_i)}{\pi L_c d(R_o + r_i)}.$$

This temperature profile will give equal flow velocities in all the separation sections in the composite column.

In the preceding examples the compensation was limited to providing equal residence times in all of the separation sections. Consider the cylindrical separation chamber 8 of FIG. 15. Sample moving near the chamber center axis will have a shorter path through the chamber than that traveling along a peripheral region. In order to show that this source of dispersion can also be compensated for, we consider a specific example consisting of the following parameters:

$R_o$=1.25 cm, $R_i$=0.25 cm, $\delta h$=0.1 cm, $\delta r$=0.1 cm,
$V_o$=10,000 V, $\mu_{wo}$=5.1×10$^{-4}$ cm$^2$/V sec,
$d_o$=0.032 cm, $d_i$=0.015 cm, $L_c$=50 cm, and
d=0.02 cm.

The Section A—A in the figure shows five separation sections or arrays 24 and six circular cooling channels 68. The temperature difference $\delta T(r_i)$ can be expressed as $$\delta T(r_i) = K \Gamma r_i \frac{(R_o - r_i)}{(R_o + r_i)}$$

where $\Gamma$ is an adjustment parameter used to equalize the residence times, and $$K = 50 \frac{\pi}{d} \frac{\delta h}{L_c} \frac{d_i^2}{d_o^2}.$$

The flow in each separation section $Qc_i$ is given by $Qc_i$=velocity×number of tubes in each section×tube area $$Qc_i = v(r_i) n(r_i) \frac{d_i^2}{4}$$

or using equations above:

$$Qc_i = \frac{V_w k r_i [1 + 0.02 \delta T(r_i)]}{1 + k_1 r_i \frac{(R_o - r_i)}{(R_o + r_i)}},$$

where $$k_1 = \frac{\pi \delta h}{d L_c} \left( \frac{d_i}{d_o} \right)^2, \text{ and } V_w = \mu_{wo} \frac{V_o}{L_c}.$$

The flow rate in the transition region is $$Qt_i = \sum_{j=i}^{5} Qc_j \text{ at each } r_i.$$

The velocity at each separation section ($r_i$) is $$v_i = \frac{Qt_i}{2\pi dr_i},$$

and the migration time between sections in the transition region is $$t_1 = \frac{2R_i}{v_1}$$

and $$t_i = \frac{2(\delta h + \delta r)}{v_{i-1} + V_i}, \quad 1 < i \leq 5.$$

The elapsed time $t_i$ required to move to $r_i$ from the center line in the transition region is $$\tau t_1 = t_1$$

and $$\tau t_i = \tau t_{i-1} + t_i.$$

The velocity in each separation section is given by $$V_i = (\mu_{wo} - \mu_e) E(r_i)[1 + 0.02 \delta T(r_i)]$$

so, $$V_i = (\mu_{wo} - \mu_e) E_o \frac{[1 + 0.02 \delta T(r_i)]}{\left[ 1 + k_1 r_i \frac{(R_o - r_i)}{(R_o + r_i)} \right]}$$

where $$E_o = \frac{V_o}{L_c}.$$

The total residence times for the sample in each separation section is $\tau_i$=time in transition chambers plus time in the $i^{th}$ separation chamber, $$\tau_i = 2\tau t_i + \frac{L_c}{V_i}$$

where the two accounts for both (top and bottom) transition chambers.

For $\Gamma$=0 and $\mu_e$=0, 1, 2, 3, 4×10$^{-4}$ cm$^{-2}$/V sec, the radial temperature distributions for exact compensation are given in FIG. 16. As the figure shows, the temperature distributions do not vary greatly with $\mu_e$, and good resolution could be achieved by using an average distribution throughout the run. If greater resolution is desired, the distribution for $\mu_e$=0 could be used until the sample ($\mu_e$=0) is eluted, then the distribution changed to provide exact compensation for $\mu_e$>0. These modified distributions would change with time and, of course, would not be the same as those shown in FIG. 16, which were averaged over the total run time. EOF in the transition region 3 would need to be suppressed to preclude interaction with the PDF which would result in unacceptable sample zone distortion. Sample migration in each transition region 3, 3' is self-compensating since the electric fields are equal and opposite.

Consider the cylindrical preparative separation chamber shown in FIG. 15. Section A—A of the chamber 8 shows the multiple annular cooling channels 68 at uniform radial intervals. By varying the coolant temperature in each channel, an arbitrary general radial temperature distribution can be maintained despite the slight increases necessarily occurring within the separation arrays 24. The temperature increases are periodic in r and result from the heat transfer to the cooling channels 68. These temperature increases in the separation arrays 24 must be limited by considerations of thermal distortion.

Note the circular electrode configuration of the chamber 8. This configuration causes a nonuniform electric field in the separation chamber 8 and the nonuniformity depends on the depth (d) of the transition section 3. If the diameter of the total chamber is large, then d must also be large to keep the voltage variation within desirable limits. Then to control and stabilize the flow in the transition section 3 we must use a stabilizing matrix. A packing of inert beads, such as glass beads 72, will serve this purpose. With the temperature field controlled by the temperature distribution in the cooling channels 68 and the voltage variation controlled by the transition section depth d, the residence time of sample moving through the capillaries 43 can be made uniform. This is a major factor in separation efficiency, especially for chambers of large diameter. The above described configurations will permit unlimited scale-up of CFFE for preparative separations.

In contrast to CZE, which is carried out in a free-fluid, packed tubes are used in electrochromatographic separations. The tubes are limited to not more than 200 μm by self-heating. Conversely, pressure-driven LC, also carried out in packed tubes, does not have such a limitation. It was thought 9 years ago[15] that electrochromatography was on the verge of massive growth and would rival conventional HPLC. This has not happened, largely due to the heating problem mandating miniaturization and the inability of the process to be completely adapted to the chromatography format. Using electrochromatography in the CFFE configuration eliminates both of these problems.

Instead of using multicapillary arrays, packed annular or flat sections could be used, as described above. The efficiency of the multisection cooling channels would eliminate heating problems and thus allow for scale-up, while the CFFE flow transducer would allow the full chromatographic operational efficiency to be realized. Due to problems in procuring economical multitube arrays, the electrochromatography option for CFFE might be the most attractive preparative application of the technology in the near future.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

REFERENCES

1. Altria, K. D., and Simpson, C. F., High Voltage Capillary Zone Electrophoresis: Operating Parameters Effects on Electroosmotic Flows and Electrophoretic Mobilities, *Chromatographia*, 24, 527–532 (1987).
2. Aris, R., On the Dispersion of a Solute in a Fluid Flowing Through a Tube, *Proc. Roy. Soc.* (London), A235, 67–77 (1955).
3. Belen'kii, B. G., Capillary Electrophoresis: New Possibilities for Analytical Chemistry (Review), *Industrial Laboratory*, 59(12), 1–13 (1993).
4. Clifton, M. J., Continuous-Flow Electrophoresis in the Taylor Regime: A New Possibility for Preparative Electrophoresis, *J. Chrom. A.*, 757, 193–202 (1997).
5. Cooke, W. S., Multicapillary Columns: An Idea whose Time has Come, *Todays Chemist at Work*, 16–20 (January 1996).
6. Davis, J. M., Influence of Thermal Variation of Diffusion Coefficient on Non-equilibrium Plate Height in Capillary Zone Electrophoresis, *J. Chrom.*, 517, 521–547 (1990).
7. Giddings, J. C., Generation of Variance, "Theoretical Plates," Resolution and Peak Capacity in Electrophoresis and Sedimentation, *Sep. Sci.*, 4(3), 181–189 (1969).
8. Gobie, W. A., and Ivory, C. F., Thermal Model of Capillary Electrophoresis and a Method for Counteracting Thermal Band Broadening, *J. Chrom.*, 516, 191–210 (1990).
9. Gordon, J. M., Lee, K. -J., Arias, A. A., and Zare, R. N., Protocol for Resolving Protein Mixtures in Capillary Zone Electrophoresis, *Anal Chem.*, 63(1), 69–72 (1991).
10. Grushka, E., McCormick, R. M., and Kirkland, J. J., Effect of Temperature Gradients on the Efficiency of Capillary Zone Electrophoresis Separations, *Anal. Chem.*, 61, 241–246 (1989).
11. Hjerten, S., Free Zone Electrophoresis, *Chromatogr. Rev.*, 9, 122–219 (1967).
12. Ivory, C. F., The Prospects for Large Scale Electrophoresis, *Sep. Sci. and Tech.*, 23(8&9), 875–912 (1988).
13. Jorgenson, J. W., and Lukacs, K. D., Capillary Zone Electrophoresis, *Science*, 222, 266–272 (1983).
14. Knox, J. H., Thermal Effects and Band Spreading in Capillary Electro-Separation, *Chromatographia*, 26, 329–337 (1988).
15. Knox, J. H., and Grant, I. W., Miniaturization in Pressure and Electroendosmotically-Driven Liquid Chromatography: Some Theoretical Considerations, *Chromatographia*, 24, 135–143 (1987).
16. Landers, J. P., Ed., *Handbook of Capillary Electrophoresis*, CRC Press, Inc. (1944).
17. Mikkers, F. E. P., Everaerts, F. M., and Verheggen, P. E. M., Concentration Distribution in Free Zone Electrophoresis, *J. Chrom.*, 169, 1–10 (1979).
18. Potocek, B., Gas, B., Kenndler, E., and Stedry, M., Electroosmosis in Capillary Zone Electrophoresis with Non-Uniform Zeta Potential, *J. Chrom. A.*, 709, 51–62 (1995).
19. Roberts, G. O., Rhodes, P. H., and Snyder, R. S., Dispersion Effects in Capillary Zone Electrophoresis, *J. Chrom.*, 480, 35–67 (1989).
20. Rose, D. J., and Jorgenson, J. W., Fraction Collector for Capillary Zone Electrophoresis, *J. Chrom.*, 438, 23–34 (1988).
21. Taylor, G. I., Dispersion of Soluble Matter in Solvent Flowing Slowly Through a Tube, *Proc. Roy. Soc.* (London), A219, 186–203 (1953).
22. Weinberger, R., Separations Solutions, American Laboratory, 33U–33V (March 1995).
23. Zhu, A. and Chen, Y., High Voltage Capillary Zone Electrophoresis of Red Blood Cells, *J. Chrom.*, 470, 251–260 (1960).

What is claimed is:

1. A method of controlling parabolic sample dispersion during free-fluid electrophoresis using a capillary having a diameter of greater than 50 microns comprising detecting parabolic sample dispersion and correcting the dispersion by instituting an imbalance between electroosmotic return flow and a pressure-induced flow.

2. A method according to claim 1 wherein free-fluid electrophoresis is performed in an apparatus having an entrance region, an inner separation region and an exit region so that free-fluid electrophoresis can be carried out using the same equipment and processes used in high performance liquid chromatography.

3. A method according to claim 2 wherein an imbalance is instituted between electroosmotic return flow in the separation region and a pressure-induced flow in the entrance region.

4. A method according to claim 2 wherein the necessary electroosmotic flow is developed in the separation region by adjusting an electric field in the separation region in combination with the pressure-induced flow in the entrance and exit regions.

5. A method according to claim 2 wherein a transducer is employed to maintain electroosmotic flow in the separation region against said pressure-induced flow in the exit and entrance regions in the absence of any dispersion.

6. A method according to claim 5 wherein the transducer comprises a chamber divided into two subchambers by an elastic membrane and wherein induced motion of the elastic membrane is used to detect a pressure difference between the subchambers and produce a signal proportional to said pressure difference.

7. A method according to claim 5 wherein output of the transducer establishes a modified electroosmotic flow in the separation section by regulating a parameter selected from the group consisting of an electric field driving the electrophoresis, a pump producing said pressure-induced flow and both the electric field and the pump.

8. A method according to claim 2 further comprising the step of characterizing real-time performance by analyzing a parameter selected from the group consisting of a tracer sample with known mobility characteristics, early eluted peaks, and both of these parameters, and modifying electroosmotic flow based on these parameters.

9. A method according to claim 2 wherein reproducibility is enhanced by adjusting the pump in the entrance region to set sample position as a function of time.

10. A method according to claim 1 wherein the controlled sample dispersion results from thermal gradients and their impact on sample mobility.

11. A method according to claim 1 wherein the controlled sample dispersion results from convection flows produced in the vertical column configuration of the free-fluid electrophoresis apparatus.

12. A free-fluid electrophoresis apparatus with controlled sample dispersion comprising a capillary having a diameter of greater than 50 microns, means for detecting parabolic sample dispersion in said capillary tube and means for correcting parabolic sample dispersion by instituting an imbalance between electroosmotic return flow and a pressure-induced flow.

13. An apparatus according to claim 12 further comprising an entrance region, an inner separation region and an exit region so that free-fluid electrophoresis can be carried out using the same equipment used in high performance liquid chromatography.

14. An apparatus according to claim 13 further comprising a flow transducer which is used to measure the imbalance between electroosmotic return flow in the inner separation region and pressure-induced flow in the entrance region.

15. An apparatus according to claim 14 wherein the flow transducer converts a pressure difference between a first conducting joint of the capillary and a second conducting joint of said capillary into a parameter which can be used to establish modified electroosmotic flow in the inner separation region.

16. An apparatus according to claim 15 wherein the electroosmotic flow is modified by an imbalance between the pressure-induced flow and electroosmotic return flow by altering a parameter selected from the group consisting of an electric field, a pump producing said pressure-induced flow and both the electric field and the pump.

17. A method for achieving electrophoretic separation of an electrically charged sample material in a fluid using a capillary having a diameter of greater than 50 microns comprising causing the fluid containing the electrically charged material to pass through an apparatus containing at least one elongate capillary chamber in which electrophoretic separation occurs, one elongate entrance chamber where pressure-driven flow exists and one elongate exit chamber where pressure-driven flow also exists and fraction collection occurs, means for inducing an electric field across the capillary chamber to induce electrophoretic movement of the electrically charged material, means for inducing a pressure driven flow in the entrance region, transducer means for maintaining only modified electroosmotic flow in the capillary chamber, and regulation means for modifying the electroosmotic flow in the capillary chamber wherein the parabolic dispersion is controlled by maintaining an imbalance between pressure-driven flow and electroosmotic flow in the capillary chamber in response to output from the transducer.

18. A method according to claim 17 wherein said transducer detects a pressure difference across the capillary chamber as delineated by electrically conducting joints.

19. A method according to claim 17 wherein the fluid containing the sample material is caused to pass through an array of capillary chambers.

20. An apparatus for achieving electrophoretic separation of an electrically charged material in a fluid using a capillary of greater than 50 microns comprising at least one elongate inner capillary chamber in which electrophoretic separation occurs; one elongate entrance chamber where pressure-driven flow is initiated and one elongate exit chamber where fraction collection occurs; means for inducing an electric field across the inner capillary chamber to induce electrophoretic movement of the electrically charged material; means for inducing pressure-driven fluid flow in the entrance region; transducer means for maintaining only modified electroosmotic flow in the inner capillary chamber; and regulation means for modifying the electroosmotic flow in the inner capillary chamber wherein parabolic dispersion is controlled by maintaining an imbalance between pressure-driven flow and electroosmotic return flow in the inner capillary chamber in response to the output from the transducer.

21. An apparatus according to claim 20 further comprising a gasket joint of a rigidly configured ion permeable membrane.

22. An apparatus according to claim 20 wherein the regulation means operates to provide electroosmotic flow in the inner capillary chamber with modification to compensate for parabolic dispersions through control of the electric field as governed by real time input from the flow transducer.

23. An apparatus according to claim 20 wherein the capillary separation chamber is replaced by an array of capillary chambers.

24. An apparatus according to claim 23 further comprising a sample injection mechanism for simultaneously inserting equal amounts of sample into equivalent positions in each chamber of the array.

25. An apparatus according to claim 23 further comprising means for controlling thermal gradients in a large-scale capillary array through cooling sections placed within the capillary arrays.

26. An apparatus according to claim 20 wherein the transducer produces modified electroosmotic flow in the inner capillary chamber by producing a real-time count which is the accumulation of the instantaneous pressure difference between one end of a section of the capillary chamber and an opposite end of said section, the count being representative of the accumulated imbalance between pressure-driven flow and electroosmotic flow in the capillary chamber.

27. An apparatus for achieving electrophoretic separation of an electrically charged material in a fluid using a capillary having a diameter greater than 50 microns comprising: at least one capillary chamber in which electrophoretic separation occurs; a pump for inducing pressure-driven fluid flow in fluid communication with an entrance region of the apparatus; a power supply and associated electrodes disposed in relation to the capillary chamber for imposing an electrical field across the capillary from a first conducting joint of the capillary to a second conducting joint of the capillary; transducer means for detecting a pressure difference across the capillary, the transducer means for maintaining only modified electroosmotic flow in said capillary chamber; and regulation means for modifying the electroosmotic flow in the capillary chamber wherein parabolic dispersion is controlled by maintaining an imbalance between pressure-driven flow and electroosmotic return flow in the separation chamber in response to output from the transducer means.

28. An apparatus according to claim 27 wherein unlimited scale-up of the preparative system is possible through the use of specific non-uniform voltage and temperature fields which ensure equal sample migration times in the sample capillaries regardless of the size of the array.

29. An apparatus according to claim 28, wherein the capillary separation chamber comprises an array of capillary tubes.

30. An electrophoresis system comprising means for controlling parabolic dispersion, at least one capillary having a diameter of greater than 50 microns, a first conducting joint and a second conducting joint in said capillary that causes electrophoresis through the capillary, means for inducing a pressure fluid flow through the capillary, and a pressure transducer that monitors the pressure difference between the first conducting joint and the second conducting joint of said capillary.

31. A system according to claim 30 wherein the transducer comprises a chamber divided into two subchambers by an elastic membrane and wherein induced motion of the elastic membrane is used to detect a pressure difference between the subchambers and produce a signal proportional to said pressure difference.

32. A system according to claim 31 further comprising electromagnets disposed on either side of the elastic membrane so as to induce the elastic membrane to oscillate in a predetermined pattern.

33. A system according to claim 32 further comprising optical reflectors disposed on either side of the elastic membrane and a light source and a light detector disposed on either side of the elastic membrane for optically determining the position of the membrane.

* * * * *